United States Patent
Jang et al.

(10) Patent No.: US 11,846,627 B2
(45) Date of Patent: Dec. 19, 2023

(54) METHOD AND COMPOSITION FOR SORTING OUT OF CELL COMPRISING A MODIFIED GENE

(71) Applicants: LART Bio Co., Ltd, Seoul (KR); Seoul National University R&DB Foundation, Seoul (KR)

(72) Inventors: Goo Jang, Seoul (KR); Gyeongmin Gim, Seoul (KR); Dong Hyeok Kwon, Seoul (KR); Wonyou Lee, Gyeonggi-do (KR)

(73) Assignees: LART BIO CO., LTD, Seoul (KR); SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 0 days.

(21) Appl. No.: 17/568,032

(22) Filed: Jan. 4, 2022

(65) Prior Publication Data
US 2022/0214327 A1 Jul. 7, 2022

(30) Foreign Application Priority Data
Jan. 4, 2021 (KR) .................. 10-2021-0000494

(51) Int. Cl.
| | | |
|---|---|---|
| G01N 33/50 | (2006.01) | |
| A01K 67/027 | (2006.01) | |
| C12N 9/22 | (2006.01) | |
| C12N 15/01 | (2006.01) | |
| C12N 15/11 | (2006.01) | |
| C12N 15/90 | (2006.01) | |

(52) U.S. Cl.
CPC ..... *G01N 33/5005* (2013.01); *A01K 67/0275* (2013.01); *C12N 9/22* (2013.01); *C12N 15/11* (2013.01); *C12N 15/907* (2013.01); *A01K 2207/12* (2013.01); *A01K 2227/101* (2013.01); *C12N 2310/20* (2017.05); *C12N 2800/80* (2013.01)

(58) Field of Classification Search
CPC .................. A01K 67/0275; C12N 2310/20
See application file for complete search history.

(56) References Cited

PUBLICATIONS

Ikeda et al (Efficient scarless genome editing in human pluripotent stem cells. Nature Methods, vol. 15, Dec. 2018) (Year: 2018).*
Barrangou et al. (Applications of CRISPR technologies in research and beyond. Nature Biotechnology, vol. 34, Sep. 2016) (Year: 2016).*
Bevacqua et al (Efficient edition of the bovine PRNP prion gene in somatic cells and IVF embryos using the CRISPR/Cas9 system. Theriogenology, vol. 86, 2016). (Year: 2016).*
Letter to the Editor, "Transgenic F2 bovine embryos show stable germline transmission and maintenance of transgene expression through two generations", Biology of Reproduction, 2020, 103(6), 1148-1151.

* cited by examiner

*Primary Examiner* — Kara D Johnson
*Assistant Examiner* — Matasha Dhar
(74) *Attorney, Agent, or Firm* — Harness, Dickey & Pierce, P.L.C.

(57) ABSTRACT

Provided is a method for more efficiently sorting out genetically modified cells. Specifically provided are a method for selecting a cell including a modified gene on a target locus in a genome, a method for producing a cell including a modified gene on a target locus in a genome, and an animal including a modified gene on a target locus in a genome, and a kit for selecting an animal including a modified gene on a target locus in a genome and cells including a modified gene on a target locus in a genome.

6 Claims, 6 Drawing Sheets
Specification includes a Sequence Listing.

(a) GFP(+)

(b) GFP(-)

(a)

(b)

F : GCTCTAGAGCCTCTGCTAA
R : CACATGAAGCAGCACGACTTC

SEQUENCE LISTING

<160> NUMBER OF SEQ ID NOS: 285

<210> SEQ ID NO 1
<211> LENGTH: 20
<212> TYPE: RNA
<213> ORGANISM: Artificial Sequence
<220> FEATURE:
<223> OTHER INFORMATION: guide sequence

<400> SEQUENCE: 1
ggagaugucg cuggccgcca                                              20

<210> SEQ ID NO 2
<211> LENGTH: 23
<212> TYPE: RNA
<213> ORGANISM: Artificial Sequence
<220> FEATURE:
<223> OTHER INFORMATION: guide sequence

<400> SEQUENCE: 2
guacuccuug gccauggcgg cca                                          23

<210> SEQ ID NO 3
<211> LENGTH: 23
<212> TYPE: RNA
<213> ORGANISM: Artificial Sequence
<220> FEATURE:
<223> OTHER INFORMATION: guide sequence

<400> SEQUENCE: 3
gccauggcgg ccagcgacau cuc                                          23

<210> SEQ ID NO 4
<211> LENGTH: 23
<212> TYPE: RNA
<213> ORGANISM: Artificial Sequence
<220> FEATURE:
<223> OTHER INFORMATION: guide sequence

<400> SEQUENCE: 4
agcuccucca cauacacucu cag                                          23

<210> SEQ ID NO 5
<211> LENGTH: 23
<212> TYPE: RNA
<213> ORGANISM: Artificial Sequence
<220> FEATURE:
<223> OTHER INFORMATION: guide sequence

<400> SEQUENCE: 5
ugcagcagga ucuccagguc gcc                                          23

<210> SEQ ID NO 6
<211> LENGTH: 23
<212> TYPE: RNA
<213> ORGANISM: Artificial Sequence
<220> FEATURE:
<223> OTHER INFORMATION: guide sequence

<400> SEQUENCE: 6
cugcagcagg aucuccaggu cgc                                          23

<210> SEQ ID NO 7

```
<211> LENGTH: 20
<212> TYPE: RNA
<213> ORGANISM: Artificial Sequence
<220> FEATURE:
<223> OTHER INFORMATION: guide sequence

<400> SEQUENCE: 7
aucaugguga aaagccacau                                                     20

<210> SEQ ID NO 8
<211> LENGTH: 20
<212> TYPE: RNA
<213> ORGANISM: Artificial Sequence
<220> FEATURE:
<223> OTHER INFORMATION: guide sequence

<400> SEQUENCE: 8
ugaaaagcca cauaggcagu                                                     20

<210> SEQ ID NO 9
<211> LENGTH: 20
<212> TYPE: RNA
<213> ORGANISM: Artificial Sequence
<220> FEATURE:
<223> OTHER INFORMATION: guide sequence

<400> SEQUENCE: 9
ccacauaggc aguuggaucc                                                     20

<210> SEQ ID NO 10
<211> LENGTH: 20
<212> TYPE: RNA
<213> ORGANISM: Artificial Sequence
<220> FEATURE:
<223> OTHER INFORMATION: guide sequence

<400> SEQUENCE: 10
ccaggaucca acugccuaug                                                     20

<210> SEQ ID NO 11
<211> LENGTH: 20
<212> TYPE: RNA
<213> ORGANISM: Artificial Sequence
<220> FEATURE:
<223> OTHER INFORMATION: guide sequence

<400> SEQUENCE: 11
uuggauccug guucucuuug                                                     20

<210> SEQ ID NO 12
<211> LENGTH: 20
<212> TYPE: RNA
<213> ORGANISM: Artificial Sequence
<220> FEATURE:
<223> OTHER INFORMATION: guide sequence

<400> SEQUENCE: 12
acauggccac aaagagaacc                                                     20

<210> SEQ ID NO 13
<211> LENGTH: 20
<212> TYPE: RNA
<213> ORGANISM: Artificial Sequence
<220> FEATURE:
<223> OTHER INFORMATION: guide sequence

<400> SEQUENCE: 13
```
ugguucucuu uguggccaug                                               20

<210> SEQ ID NO 14
<211> LENGTH: 20
<212> TYPE: RNA
<213> ORGANISM: Artificial Sequence
<220> FEATURE:
<223> OTHER INFORMATION: guide sequence

<400> SEQUENCE: 14
uguggccaug uggagugacg                                               20

<210> SEQ ID NO 15
<211> LENGTH: 20
<212> TYPE: RNA
<213> ORGANISM: Artificial Sequence
<220> FEATURE:
<223> OTHER INFORMATION: guide sequence

<400> SEQUENCE: 15
guggccaugu ggagugacgu                                               20

<210> SEQ ID NO 16
<211> LENGTH: 20
<212> TYPE: RNA
<213> ORGANISM: Artificial Sequence
<220> FEATURE:
<223> OTHER INFORMATION: guide sequence

<400> SEQUENCE: 16
gaggcccacg ucacuccaca                                               20

<210> SEQ ID NO 17
<211> LENGTH: 20
<212> TYPE: RNA
<213> ORGANISM: Artificial Sequence
<220> FEATURE:
<223> OTHER INFORMATION: guide sequence

<400> SEQUENCE: 17
guuuuggucg cuucuugcag                                               20

<210> SEQ ID NO 18
<211> LENGTH: 20
<212> TYPE: RNA
<213> ORGANISM: Artificial Sequence
<220> FEATURE:
<223> OTHER INFORMATION: guide sequence

<400> SEQUENCE: 18
ugcaagaagc gaccaaaacc                                               20

<210> SEQ ID NO 19
<211> LENGTH: 20
<212> TYPE: RNA
<213> ORGANISM: Artificial Sequence
<220> FEATURE:
<223> OTHER INFORMATION: guide sequence

<400> SEQUENCE: 19
aagaagcgac caaaaccugg                                               20

<210> SEQ ID NO 20
<211> LENGTH: 20
<212> TYPE: RNA

```
<213> ORGANISM: Artificial Sequence
<220> FEATURE:
<223> OTHER INFORMATION: guide sequence

<400> SEQUENCE: 20
aagcgaccaa aaccuggagg                                                    20

<210> SEQ ID NO 21
<211> LENGTH: 20
<212> TYPE: RNA
<213> ORGANISM: Artificial Sequence
<220> FEATURE:
<223> OTHER INFORMATION: guide sequence

<400> SEQUENCE: 21
gaccaaaacc uggaggagga                                                    20

<210> SEQ ID NO 22
<211> LENGTH: 20
<212> TYPE: RNA
<213> ORGANISM: Artificial Sequence
<220> FEATURE:
<223> OTHER INFORMATION: guide sequence

<400> SEQUENCE: 22
uuccauccuc cuccagguuu                                                    20

<210> SEQ ID NO 23
<211> LENGTH: 20
<212> TYPE: RNA
<213> ORGANISM: Artificial Sequence
<220> FEATURE:
<223> OTHER INFORMATION: guide sequence

<400> SEQUENCE: 23
ccuggaggag gauggaacac                                                    20

<210> SEQ ID NO 24
<211> LENGTH: 20
<212> TYPE: RNA
<213> ORGANISM: Artificial Sequence
<220> FEATURE:
<223> OTHER INFORMATION: guide sequence

<400> SEQUENCE: 24
ccaguguucc auccuccucc                                                    20

<210> SEQ ID NO 25
<211> LENGTH: 20
<212> TYPE: RNA
<213> ORGANISM: Artificial Sequence
<220> FEATURE:
<223> OTHER INFORMATION: guide sequence

<400> SEQUENCE: 25
cuggaggagg auggaacacu                                                    20

<210> SEQ ID NO 26
<211> LENGTH: 20
<212> TYPE: RNA
<213> ORGANISM: Artificial Sequence
<220> FEATURE:
<223> OTHER INFORMATION: guide sequence

<400> SEQUENCE: 26
uggaggagga uggaacacug                                                    20
```

<210> SEQ ID NO 27
<211> LENGTH: 20
<212> TYPE: RNA
<213> ORGANISM: Artificial Sequence
<220> FEATURE:
<223> OTHER INFORMATION: guide sequence

<400> SEQUENCE: 27
ggaggaggau ggaacacugg                                               20

<210> SEQ ID NO 28
<211> LENGTH: 20
<212> TYPE: RNA
<213> ORGANISM: Artificial Sequence
<220> FEATURE:
<223> OTHER INFORMATION: guide sequence

<400> SEQUENCE: 28
gaggaggaug gaacacuggg                                               20

<210> SEQ ID NO 29
<211> LENGTH: 20
<212> TYPE: RNA
<213> ORGANISM: Artificial Sequence
<220> FEATURE:
<223> OTHER INFORMATION: guide sequence

<400> SEQUENCE: 29 acuggggga gccgauaccc                                                20

<210> SEQ ID NO 30
<211> LENGTH: 20
<212> TYPE: RNA
<213> ORGANISM: Artificial Sequence
<220> FEATURE:
<223> OTHER INFORMATION: guide sequence

<400> SEQUENCE: 30
ggggagccga uacccaggac                                               20

<210> SEQ ID NO 31
<211> LENGTH: 20
<212> TYPE: RNA
<213> ORGANISM: Artificial Sequence
<220> FEATURE:
<223> OTHER INFORMATION: guide sequence

<400> SEQUENCE: 31
gggagccgau acccaggaca                                               20

<210> SEQ ID NO 32
<211> LENGTH: 20
<212> TYPE: RNA
<213> ORGANISM: Artificial Sequence
<220> FEATURE:
<223> OTHER INFORMATION: guide sequence

<400> SEQUENCE: 32
gacugcccug uccuggguau                                               20

<210> SEQ ID NO 33
<211> LENGTH: 20
<212> TYPE: RNA
<213> ORGANISM: Artificial Sequence
<220> FEATURE:

```
<223> OTHER INFORMATION: guide sequence

<400> SEQUENCE: 33
uacccaggac agggcagucc                                               20

<210> SEQ ID NO 34
<211> LENGTH: 20
<212> TYPE: RNA
<213> ORGANISM: Artificial Sequence
<220> FEATURE:
<223> OTHER INFORMATION: guide sequence

<400> SEQUENCE: 34
cuccaggacu gcccuguccu                                               20

<210> SEQ ID NO 35
<211> LENGTH: 20
<212> TYPE: RNA
<213> ORGANISM: Artificial Sequence
<220> FEATURE:
<223> OTHER INFORMATION: guide sequence

<400> SEQUENCE: 35
ccaggacagg gcaguccugg                                               20

<210> SEQ ID NO 36
<211> LENGTH: 20
<212> TYPE: RNA
<213> ORGANISM: Artificial Sequence
<220> FEATURE:
<223> OTHER INFORMATION: guide sequence

<400> SEQUENCE: 36
ccuccaggac ugcccugucc                                               20

<210> SEQ ID NO 37
<211> LENGTH: 20
<212> TYPE: RNA
<213> ORGANISM: Artificial Sequence
<220> FEATURE:
<223> OTHER INFORMATION: guide sequence

<400> SEQUENCE: 37
gguggauaac gguugccucc                                               20

<210> SEQ ID NO 38
<211> LENGTH: 20
<212> TYPE: RNA
<213> ORGANISM: Artificial Sequence
<220> FEATURE:
<223> OTHER INFORMATION: guide sequence

<400> SEQUENCE: 38
aggcaaccgu uauccaccuc                                               20

<210> SEQ ID NO 39
<211> LENGTH: 20
<212> TYPE: RNA
<213> ORGANISM: Artificial Sequence
<220> FEATURE:
<223> OTHER INFORMATION: guide sequence

<400> SEQUENCE: 39
ggcaaccguu auccaccuca                                               20
```

-continued

<210> SEQ ID NO 40
<211> LENGTH: 20
<212> TYPE: RNA
<213> ORGANISM: Artificial Sequence
<220> FEATURE:
<223> OTHER INFORMATION: guide sequence

<400> SEQUENCE: 40
aaccguuauc caccucaggg                                    20

<210> SEQ ID NO 41
<211> LENGTH: 20
<212> TYPE: RNA
<213> ORGANISM: Artificial Sequence
<220> FEATURE:
<223> OTHER INFORMATION: guide sequence

<400> SEQUENCE: 41
accguuaucc accucaggga                                    20

<210> SEQ ID NO 42
<211> LENGTH: 20
<212> TYPE: RNA
<213> ORGANISM: Artificial Sequence
<220> FEATURE:
<223> OTHER INFORMATION: guide sequence

<400> SEQUENCE: 42
ccguuaucca ccucagggag                                    20

<210> SEQ ID NO 43
<211> LENGTH: 20
<212> TYPE: RNA
<213> ORGANISM: Artificial Sequence
<220> FEATURE:
<223> OTHER INFORMATION: guide sequence

<400> SEQUENCE: 43
ccccucccug agguggauaa                                    20

<210> SEQ ID NO 44
<211> LENGTH: 20
<212> TYPE: RNA
<213> ORGANISM: Artificial Sequence
<220> FEATURE:
<223> OTHER INFORMATION: guide sequence

<400> SEQUENCE: 44
cguuauccac cucagggagg                                    20

<210> SEQ ID NO 45
<211> LENGTH: 20
<212> TYPE: RNA
<213> ORGANISM: Artificial Sequence
<220> FEATURE:
<223> OTHER INFORMATION: guide sequence

<400> SEQUENCE: 45
uauccaccuc agggagggggg                                   20

<210> SEQ ID NO 46
<211> LENGTH: 20
<212> TYPE: RNA
<213> ORGANISM: Artificial Sequence
<220> FEATURE:
<223> OTHER INFORMATION: guide sequence

```
<400> SEQUENCE: 46
cagccacccc cucccugagg                                               20

<210> SEQ ID NO 47
<211> LENGTH: 20
<212> TYPE: RNA
<213> ORGANISM: Artificial Sequence
<220> FEATURE:
<223> OTHER INFORMATION: guide sequence

<400> SEQUENCE: 47
caccucaggg aggggguggc                                               20

<210> SEQ ID NO 48
<211> LENGTH: 20
<212> TYPE: RNA
<213> ORGANISM: Artificial Sequence
<220> FEATURE:
<223> OTHER INFORMATION: guide sequence

<400> SEQUENCE: 48
accucaggga gggguggcu                                                20

<210> SEQ ID NO 49
<211> LENGTH: 20
<212> TYPE: RNA
<213> ORGANISM: Artificial Sequence
<220> FEATURE:
<223> OTHER INFORMATION: guide sequence

<400> SEQUENCE: 49
ccucagggag ggguggcug                                                20

<210> SEQ ID NO 50
<211> LENGTH: 20
<212> TYPE: RNA
<213> ORGANISM: Artificial Sequence
<220> FEATURE:
<223> OTHER INFORMATION: guide sequence

<400> SEQUENCE: 50
ccccagccac ccccucccug                                               20

<210> SEQ ID NO 51
<211> LENGTH: 20
<212> TYPE: RNA
<213> ORGANISM: Artificial Sequence
<220> FEATURE:
<223> OTHER INFORMATION: guide sequence

<400> SEQUENCE: 51
gguggcuggg gucagcccca                                               20

<210> SEQ ID NO 52
<211> LENGTH: 20
<212> TYPE: RNA
<213> ORGANISM: Artificial Sequence
<220> FEATURE:
<223> OTHER INFORMATION: guide sequence

<400> SEQUENCE: 52
ggcugggguc agccccaugg                                               20

<210> SEQ ID NO 53
<211> LENGTH: 20
```

```
<212> TYPE: RNA
<213> ORGANISM: Artificial Sequence
<220> FEATURE:
<223> OTHER INFORMATION: guide sequence

<400> SEQUENCE: 53
uggggucagc cccauggagg                                               20

<210> SEQ ID NO 54
<211> LENGTH: 20
<212> TYPE: RNA
<213> ORGANISM: Artificial Sequence
<220> FEATURE:
<223> OTHER INFORMATION: guide sequence

<400> SEQUENCE: 54
gucagcccca uggagguggc                                               20

<210> SEQ ID NO 55
<211> LENGTH: 20
<212> TYPE: RNA
<213> ORGANISM: Artificial Sequence
<220> FEATURE:
<223> OTHER INFORMATION: guide sequence

<400> SEQUENCE: 55
ucagccccau ggagguggcu                                               20

<210> SEQ ID NO 56
<211> LENGTH: 20
<212> TYPE: RNA
<213> ORGANISM: Artificial Sequence
<220> FEATURE:
<223> OTHER INFORMATION: guide sequence

<400> SEQUENCE: 56
cagccccaug gagguggcug                                               20

<210> SEQ ID NO 57
<211> LENGTH: 20
<212> TYPE: RNA
<213> ORGANISM: Artificial Sequence
<220> FEATURE:
<223> OTHER INFORMATION: guide sequence

<400> SEQUENCE: 57
uggccccagc caccuccaug                                               20

<210> SEQ ID NO 58
<211> LENGTH: 20
<212> TYPE: RNA
<213> ORGANISM: Artificial Sequence
<220> FEATURE:
<223> OTHER INFORMATION: guide sequence

<400> SEQUENCE: 58
cuggccccag ccaccuccau                                               20

<210> SEQ ID NO 59
<211> LENGTH: 20
<212> TYPE: RNA
<213> ORGANISM: Artificial Sequence
<220> FEATURE:
<223> OTHER INFORMATION: guide sequence

<400> SEQUENCE: 59
```
gcuggcccca gccaccucca                                              20

<210> SEQ ID NO 60
<211> LENGTH: 20
<212> TYPE: RNA
<213> ORGANISM: Artificial Sequence
<220> FEATURE:
<223> OTHER INFORMATION: guide sequence

<400> SEQUENCE: 60
gguggcuggg gccagccuca                                              20

<210> SEQ ID NO 61
<211> LENGTH: 20
<212> TYPE: RNA
<213> ORGANISM: Artificial Sequence
<220> FEATURE:
<223> OTHER INFORMATION: guide sequence

<400> SEQUENCE: 61
ggcuggggcc agccucaugg                                              20

<210> SEQ ID NO 62
<211> LENGTH: 20
<212> TYPE: RNA
<213> ORGANISM: Artificial Sequence
<220> FEATURE:
<223> OTHER INFORMATION: guide sequence

<400> SEQUENCE: 62
uggggccagc cucauggagg                                              20

<210> SEQ ID NO 63
<211> LENGTH: 20
<212> TYPE: RNA
<213> ORGANISM: Artificial Sequence
<220> FEATURE:
<223> OTHER INFORMATION: guide sequence

<400> SEQUENCE: 63
gccagccuca uggagguggc                                              20

<210> SEQ ID NO 64
<211> LENGTH: 20
<212> TYPE: RNA
<213> ORGANISM: Artificial Sequence
<220> FEATURE:
<223> OTHER INFORMATION: guide sequence

<400> SEQUENCE: 64
ccagccucau ggagguggcu                                              20

<210> SEQ ID NO 65
<211> LENGTH: 20
<212> TYPE: RNA
<213> ORGANISM: Artificial Sequence
<220> FEATURE:
<223> OTHER INFORMATION: guide sequence

<400> SEQUENCE: 65
cccagccacc uccaugaggc                                              20

<210> SEQ ID NO 66
<211> LENGTH: 20
<212> TYPE: RNA
<213> ORGANISM: Artificial Sequence

```
<220> FEATURE:
<223> OTHER INFORMATION: guide sequence

<400> SEQUENCE: 66
cagccucaug gagguggcug                                                     20

<210> SEQ ID NO 67
<211> LENGTH: 20
<212> TYPE: RNA
<213> ORGANISM: Artificial Sequence
<220> FEATURE:
<223> OTHER INFORMATION: guide sequence

<400> SEQUENCE: 67
uggccccagc caccuccaug                                                     20

<210> SEQ ID NO 68
<211> LENGTH: 20
<212> TYPE: RNA
<213> ORGANISM: Artificial Sequence
<220> FEATURE:
<223> OTHER INFORMATION: guide sequence

<400> SEQUENCE: 68
gguggcuggg gccagccuca                                                     20

<210> SEQ ID NO 69
<211> LENGTH: 20
<212> TYPE: RNA
<213> ORGANISM: Artificial Sequence
<220> FEATURE:
<223> OTHER INFORMATION: guide sequence

<400> SEQUENCE: 69
ggcuggggcc agccucaugg                                                     20

<210> SEQ ID NO 70
<211> LENGTH: 20
<212> TYPE: RNA
<213> ORGANISM: Artificial Sequence
<220> FEATURE:
<223> OTHER INFORMATION: guide sequence

<400> SEQUENCE: 70
uggggccagc cucauggagg                                                     20

<210> SEQ ID NO 71
<211> LENGTH: 20
<212> TYPE: RNA
<213> ORGANISM: Artificial Sequence
<220> FEATURE:
<223> OTHER INFORMATION: guide sequence

<400> SEQUENCE: 71
gccagccuca uggagguggc                                                     20

<210> SEQ ID NO 72
<211> LENGTH: 20
<212> TYPE: RNA
<213> ORGANISM: Artificial Sequence
<220> FEATURE:
<223> OTHER INFORMATION: guide sequence

<400> SEQUENCE: 72
ccagccucau ggagguggcu                                                     20
```

```
<210> SEQ ID NO 73
<211> LENGTH: 20
<212> TYPE: RNA
<213> ORGANISM: Artificial Sequence
<220> FEATURE:
<223> OTHER INFORMATION: guide sequence

<400> SEQUENCE: 73
cccagccacc uccaugaggc                                                  20

<210> SEQ ID NO 74
<211> LENGTH: 20
<212> TYPE: RNA
<213> ORGANISM: Artificial Sequence
<220> FEATURE:
<223> OTHER INFORMATION: guide sequence

<400> SEQUENCE: 74
cagccucaug gagguggcug                                                  20

<210> SEQ ID NO 75
<211> LENGTH: 20
<212> TYPE: RNA
<213> ORGANISM: Artificial Sequence
<220> FEATURE:
<223> OTHER INFORMATION: guide sequence

<400> SEQUENCE: 75
ugaccccagc caccuccaug                                                  20

<210> SEQ ID NO 76
<211> LENGTH: 20
<212> TYPE: RNA
<213> ORGANISM: Artificial Sequence
<220> FEATURE:
<223> OTHER INFORMATION: guide sequence

<400> SEQUENCE: 76
gguggcuggg gucagcccca                                                  20

<210> SEQ ID NO 77
<211> LENGTH: 20
<212> TYPE: RNA
<213> ORGANISM: Artificial Sequence
<220> FEATURE:
<223> OTHER INFORMATION: guide sequence

<400> SEQUENCE: 77
ggcugggguc agccccaugg                                                  20

<210> SEQ ID NO 78
<211> LENGTH: 20
<212> TYPE: RNA
<213> ORGANISM: Artificial Sequence
<220> FEATURE:
<223> OTHER INFORMATION: guide sequence

<400> SEQUENCE: 78
uggggucagc cccauggugg                                                  20

<210> SEQ ID NO 79
<211> LENGTH: 20
<212> TYPE: RNA
<213> ORGANISM: Artificial Sequence
<220> FEATURE:
<223> OTHER INFORMATION: guide sequence
```

```
<400> SEQUENCE: 79
gucagcccca uggugguggc                                               20

<210> SEQ ID NO 80
<211> LENGTH: 20
<212> TYPE: RNA
<213> ORGANISM: Artificial Sequence
<220> FEATURE:
<223> OTHER INFORMATION: guide sequence

<400> SEQUENCE: 80
ucagccccau ggugguggcu                                               20

<210> SEQ ID NO 81
<211> LENGTH: 20
<212> TYPE: RNA
<213> ORGANISM: Artificial Sequence
<220> FEATURE:
<223> OTHER INFORMATION: guide sequence

<400> SEQUENCE: 81
cagccccaug gugguggcug                                               20

<210> SEQ ID NO 82
<211> LENGTH: 20
<212> TYPE: RNA
<213> ORGANISM: Artificial Sequence
<220> FEATURE:
<223> OTHER INFORMATION: guide sequence

<400> SEQUENCE: 82 ugucccagc caccaccaug                                                20

<210> SEQ ID NO 83
<211> LENGTH: 20
<212> TYPE: RNA
<213> ORGANISM: Artificial Sequence
<220> FEATURE:
<223> OTHER INFORMATION: guide sequence

<400> SEQUENCE: 83
cuguccccag ccaccaccau                                               20

<210> SEQ ID NO 84
<211> LENGTH: 20
<212> TYPE: RNA
<213> ORGANISM: Artificial Sequence
<220> FEATURE:
<223> OTHER INFORMATION: guide sequence

<400> SEQUENCE: 84 gcuguccca gccaccacca                                                20

<210> SEQ ID NO 85
<211> LENGTH: 20
<212> TYPE: RNA
<213> ORGANISM: Artificial Sequence
<220> FEATURE:
<223> OTHER INFORMATION: guide sequence

<400> SEQUENCE: 85
gguggcuggg gacagccaca                                               20

<210> SEQ ID NO 86
```

```
<211> LENGTH: 20
<212> TYPE: RNA
<213> ORGANISM: Artificial Sequence
<220> FEATURE:
<223> OTHER INFORMATION: guide sequence

<400> SEQUENCE: 86
ggcuggggac agccacaugg                                               20

<210> SEQ ID NO 87
<211> LENGTH: 20
<212> TYPE: RNA
<213> ORGANISM: Artificial Sequence
<220> FEATURE:
<223> OTHER INFORMATION: guide sequence

<400> SEQUENCE: 87 ugggggacagc cacauggugg                                              20

<210> SEQ ID NO 88
<211> LENGTH: 20
<212> TYPE: RNA
<213> ORGANISM: Artificial Sequence
<220> FEATURE:
<223> OTHER INFORMATION: guide sequence

<400> SEQUENCE: 88
ggacagccac augguggugg                                               20

<210> SEQ ID NO 89
<211> LENGTH: 20
<212> TYPE: RNA
<213> ORGANISM: Artificial Sequence
<220> FEATURE:
<223> OTHER INFORMATION: guide sequence

<400> SEQUENCE: 89
agccacaugg ugguggaggc                                               20

<210> SEQ ID NO 90
<211> LENGTH: 20
<212> TYPE: RNA
<213> ORGANISM: Artificial Sequence
<220> FEATURE:
<223> OTHER INFORMATION: guide sequence

<400> SEQUENCE: 90
gccacauggu gguggaggcu                                               20

<210> SEQ ID NO 91
<211> LENGTH: 20
<212> TYPE: RNA
<213> ORGANISM: Artificial Sequence
<220> FEATURE:
<223> OTHER INFORMATION: guide sequence

<400> SEQUENCE: 91
ccacauggug guggaggcug                                               20

<210> SEQ ID NO 92
<211> LENGTH: 20
<212> TYPE: RNA
<213> ORGANISM: Artificial Sequence
<220> FEATURE:
<223> OTHER INFORMATION: guide sequence

<400> SEQUENCE: 92
```

```
ccccagccuc caccaccaug                                                      20

<210> SEQ ID NO 93
<211> LENGTH: 20
<212> TYPE: RNA
<213> ORGANISM: Artificial Sequence
<220> FEATURE:
<223> OTHER INFORMATION: guide sequence

<400> SEQUENCE: 93
ggugguggag gcugggguca                                                      20

<210> SEQ ID NO 94
<211> LENGTH: 20
<212> TYPE: RNA
<213> ORGANISM: Artificial Sequence
<220> FEATURE:
<223> OTHER INFORMATION: guide sequence

<400> SEQUENCE: 94
gguggaggcu gggucaagg                                                       20

<210> SEQ ID NO 95
<211> LENGTH: 20
<212> TYPE: RNA
<213> ORGANISM: Artificial Sequence
<220> FEATURE:
<223> OTHER INFORMATION: guide sequence

<400> SEQUENCE: 95
uggggucaag gugguaccca                                                      20

<210> SEQ ID NO 96
<211> LENGTH: 20
<212> TYPE: RNA
<213> ORGANISM: Artificial Sequence
<220> FEATURE:
<223> OTHER INFORMATION: guide sequence

<400> SEQUENCE: 96
aaggugguac ccacggucaa                                                      20

<210> SEQ ID NO 97
<211> LENGTH: 20
<212> TYPE: RNA
<213> ORGANISM: Artificial Sequence
<220> FEATURE:
<223> OTHER INFORMATION: guide sequence

<400> SEQUENCE: 97
ggguuuguuc cauugaccgu                                                      20

<210> SEQ ID NO 98
<211> LENGTH: 20
<212> TYPE: RNA
<213> ORGANISM: Artificial Sequence
<220> FEATURE:
<223> OTHER INFORMATION: guide sequence

<400> SEQUENCE: 98
uggguuuguu ccauugaccg                                                      20

<210> SEQ ID NO 99
<211> LENGTH: 20
<212> TYPE: RNA
```

-continued

```
<213> ORGANISM: Artificial Sequence
<220> FEATURE:
<223> OTHER INFORMATION: guide sequence

<400> SEQUENCE: 99
auguugguuu uuggcuuacu                                                     20

<210> SEQ ID NO 100
<211> LENGTH: 20
<212> TYPE: RNA
<213> ORGANISM: Artificial Sequence
<220> FEATURE:
<223> OTHER INFORMATION: guide sequence

<400> SEQUENCE: 100
cauguugguu uuuggcuuac                                                     20

<210> SEQ ID NO 101
<211> LENGTH: 20
<212> TYPE: RNA
<213> ORGANISM: Artificial Sequence
<220> FEATURE:
<223> OTHER INFORMATION: guide sequence

<400> SEQUENCE: 101
acaugcuuca uguugguuuu                                                     20

<210> SEQ ID NO 102
<211> LENGTH: 20
<212> TYPE: RNA
<213> ORGANISM: Artificial Sequence
<220> FEATURE:
<223> OTHER INFORMATION: guide sequence

<400> SEQUENCE: 102
aaaaaccaac augaagcaug                                                     20

<210> SEQ ID NO 103
<211> LENGTH: 20
<212> TYPE: RNA
<213> ORGANISM: Artificial Sequence
<220> FEATURE:
<223> OTHER INFORMATION: guide sequence

<400> SEQUENCE: 103
accaacauga agcauguggc                                                     20

<210> SEQ ID NO 104
<211> LENGTH: 20
<212> TYPE: RNA
<213> ORGANISM: Artificial Sequence
<220> FEATURE:
<223> OTHER INFORMATION: guide sequence

<400> SEQUENCE: 104
uccugccaca ugcuucaugu                                                     20

<210> SEQ ID NO 105
<211> LENGTH: 20
<212> TYPE: RNA
<213> ORGANISM: Artificial Sequence
<220> FEATURE:
<223> OTHER INFORMATION: guide sequence

<400> SEQUENCE: 105
guggcaggag cugcugcagc                                                     20
```

<210> SEQ ID NO 106
<211> LENGTH: 20
<212> TYPE: RNA
<213> ORGANISM: Artificial Sequence
<220> FEATURE:
<223> OTHER INFORMATION: guide sequence

<400> SEQUENCE: 106
agcugcugca gcuggagcag                                                  20

<210> SEQ ID NO 107
<211> LENGTH: 20
<212> TYPE: RNA
<213> ORGANISM: Artificial Sequence
<220> FEATURE:
<223> OTHER INFORMATION: guide sequence

<400> SEQUENCE: 107
gcugcagcug gagcaguggu                                                  20

<210> SEQ ID NO 108
<211> LENGTH: 20
<212> TYPE: RNA
<213> ORGANISM: Artificial Sequence
<220> FEATURE:
<223> OTHER INFORMATION: guide sequence

<400> SEQUENCE: 108
cugcagcugg agcaguggua                                                  20

<210> SEQ ID NO 109
<211> LENGTH: 20
<212> TYPE: RNA
<213> ORGANISM: Artificial Sequence
<220> FEATURE:
<223> OTHER INFORMATION: guide sequence

<400> SEQUENCE: 109
ugcagcugga gcagugguag                                                  20

<210> SEQ ID NO 110
<211> LENGTH: 20
<212> TYPE: RNA
<213> ORGANISM: Artificial Sequence
<220> FEATURE:
<223> OTHER INFORMATION: guide sequence

<400> SEQUENCE: 110
gcagcuggag cagugguagg                                                  20

<210> SEQ ID NO 111
<211> LENGTH: 20
<212> TYPE: RNA
<213> ORGANISM: Artificial Sequence
<220> FEATURE:
<223> OTHER INFORMATION: guide sequence

<400> SEQUENCE: 111
ggagcagugg uaggggggccu                                                 20

<210> SEQ ID NO 112
<211> LENGTH: 20
<212> TYPE: RNA
<213> ORGANISM: Artificial Sequence
<220> FEATURE:

<223> OTHER INFORMATION: guide sequence

<400> SEQUENCE: 112
gcagugguag ggggccuugg                                          20

<210> SEQ ID NO 113
<211> LENGTH: 20
<212> TYPE: RNA
<213> ORGANISM: Artificial Sequence
<220> FEATURE:
<223> OTHER INFORMATION: guide sequence

<400> SEQUENCE: 113
gggccuuggu ggcuacaugc                                          20

<210> SEQ ID NO 114
<211> LENGTH: 20
<212> TYPE: RNA
<213> ORGANISM: Artificial Sequence
<220> FEATURE:
<223> OTHER INFORMATION: guide sequence

<400> SEQUENCE: 114
ggccuuggug gcuacaugcu                                          20

<210> SEQ ID NO 115
<211> LENGTH: 20
<212> TYPE: RNA
<213> ORGANISM: Artificial Sequence
<220> FEATURE:
<223> OTHER INFORMATION: guide sequence

<400> SEQUENCE: 115
uucccagcau guagccacca                                          20

<210> SEQ ID NO 116
<211> LENGTH: 20
<212> TYPE: RNA
<213> ORGANISM: Artificial Sequence
<220> FEATURE:
<223> OTHER INFORMATION: guide sequence

<400> SEQUENCE: 116
ugcugggaag ugccaugagc                                          20

<210> SEQ ID NO 117
<211> LENGTH: 20
<212> TYPE: RNA
<213> ORGANISM: Artificial Sequence
<220> FEATURE:
<223> OTHER INFORMATION: guide sequence

<400> SEQUENCE: 117
auguauaaga ggccugcuca                                          20

<210> SEQ ID NO 118
<211> LENGTH: 20
<212> TYPE: RNA
<213> ORGANISM: Artificial Sequence
<220> FEATURE:
<223> OTHER INFORMATION: guide sequence

<400> SEQUENCE: 118
agcaggccuc uuauacauuu                                          20

```
<210> SEQ ID NO 119
<211> LENGTH: 20
<212> TYPE: RNA
<213> ORGANISM: Artificial Sequence
<220> FEATURE:
<223> OTHER INFORMATION: guide sequence

<400> SEQUENCE: 119
ucacugccaa aauguauaag                                          20

<210> SEQ ID NO 120
<211> LENGTH: 20
<212> TYPE: RNA
<213> ORGANISM: Artificial Sequence
<220> FEATURE:
<223> OTHER INFORMATION: guide sequence

<400> SEQUENCE: 120
acauuuuggc agugacuaug                                          20

<210> SEQ ID NO 121
<211> LENGTH: 20
<212> TYPE: RNA
<213> ORGANISM: Artificial Sequence
<220> FEATURE:
<223> OTHER INFORMATION: guide sequence

<400> SEQUENCE: 121
gcauguuuuc acgauaguaa                                          20

<210> SEQ ID NO 122
<211> LENGTH: 20
<212> TYPE: RNA
<213> ORGANISM: Artificial Sequence
<220> FEATURE:
<223> OTHER INFORMATION: guide sequence

<400> SEQUENCE: 122
aguacacuug guuggguaa                                           20

<210> SEQ ID NO 123
<211> LENGTH: 20
<212> TYPE: RNA
<213> ORGANISM: Artificial Sequence
<220> FEATURE:
<223> OTHER INFORMATION: guide sequence

<400> SEQUENCE: 123
accccaacca aguguacuac                                          20

<210> SEQ ID NO 124
<211> LENGTH: 20
<212> TYPE: RNA
<213> ORGANISM: Artificial Sequence
<220> FEATURE:
<223> OTHER INFORMATION: guide sequence

<400> SEQUENCE: 124
gccuguagua cacuugguug                                          20

<210> SEQ ID NO 125
<211> LENGTH: 20
<212> TYPE: RNA
<213> ORGANISM: Artificial Sequence
<220> FEATURE:
<223> OTHER INFORMATION: guide sequence
```

<400> SEQUENCE: 125
ggccuguagu acacuugguu                                          20

<210> SEQ ID NO 126
<211> LENGTH: 20
<212> TYPE: RNA
<213> ORGANISM: Artificial Sequence
<220> FEATURE:
<223> OTHER INFORMATION: guide sequence

<400> SEQUENCE: 126
uggccuguag uacacuuggu                                          20

<210> SEQ ID NO 127
<211> LENGTH: 20
<212> TYPE: RNA
<213> ORGANISM: Artificial Sequence
<220> FEATURE:
<223> OTHER INFORMATION: guide sequence

<400> SEQUENCE: 127
ccaaguguac uacaggccag                                          20

<210> SEQ ID NO 128
<211> LENGTH: 20
<212> TYPE: RNA
<213> ORGANISM: Artificial Sequence
<220> FEATURE:
<223> OTHER INFORMATION: guide sequence

<400> SEQUENCE: 128
ccacuggccu guaguacacu                                          20

<210> SEQ ID NO 129
<211> LENGTH: 20
<212> TYPE: RNA
<213> ORGANISM: Artificial Sequence
<220> FEATURE:
<223> OTHER INFORMATION: guide sequence

<400> SEQUENCE: 129
ugguuacuau acugauccac                                          20

<210> SEQ ID NO 130
<211> LENGTH: 20
<212> TYPE: RNA
<213> ORGANISM: Artificial Sequence
<220> FEATURE:
<223> OTHER INFORMATION: guide sequence

<400> SEQUENCE: 130
agucaugcac aaaguuguuc                                          20

<210> SEQ ID NO 131
<211> LENGTH: 20
<212> TYPE: RNA
<213> ORGANISM: Artificial Sequence
<220> FEATURE:
<223> OTHER INFORMATION: guide sequence

<400> SEQUENCE: 131
cugugucaac aucacaguca                                          20

<210> SEQ ID NO 132
<211> LENGTH: 20

```
<212> TYPE: RNA
<213> ORGANISM: Artificial Sequence
<220> FEATURE:
<223> OTHER INFORMATION: guide sequence

<400> SEQUENCE: 132
cacagucacc accaccacca                                              20

<210> SEQ ID NO 133
<211> LENGTH: 20
<212> TYPE: RNA
<213> ORGANISM: Artificial Sequence
<220> FEATURE:
<223> OTHER INFORMATION: guide sequence

<400> SEQUENCE: 133
acagucacca ccaccaccaa                                              20

<210> SEQ ID NO 134
<211> LENGTH: 20
<212> TYPE: RNA
<213> ORGANISM: Artificial Sequence
<220> FEATURE:
<223> OTHER INFORMATION: guide sequence

<400> SEQUENCE: 134
cagucaccac caccaccaag                                              20

<210> SEQ ID NO 135
<211> LENGTH: 20
<212> TYPE: RNA
<213> ORGANISM: Artificial Sequence
<220> FEATURE:
<223> OTHER INFORMATION: guide sequence

<400> SEQUENCE: 135
agucaccacc accaccaagg                                              20

<210> SEQ ID NO 136
<211> LENGTH: 20
<212> TYPE: RNA
<213> ORGANISM: Artificial Sequence
<220> FEATURE:
<223> OTHER INFORMATION: guide sequence

<400> SEQUENCE: 136 guucucccce uugguggugg                                              20

<210> SEQ ID NO 137
<211> LENGTH: 20
<212> TYPE: RNA
<213> ORGANISM: Artificial Sequence
<220> FEATURE:
<223> OTHER INFORMATION: guide sequence

<400> SEQUENCE: 137
gaaguucucc cccuuggugg                                              20

<210> SEQ ID NO 138
<211> LENGTH: 20
<212> TYPE: RNA
<213> ORGANISM: Artificial Sequence
<220> FEATURE:
<223> OTHER INFORMATION: guide sequence

<400> SEQUENCE: 138
```

-continued

```
ggugaaguuc uccccuugg                                                    20

<210> SEQ ID NO 139
<211> LENGTH: 20
<212> TYPE: RNA
<213> ORGANISM: Artificial Sequence
<220> FEATURE:
<223> OTHER INFORMATION: guide sequence

<400> SEQUENCE: 139
uucggugaag uucuccccu                                                    20

<210> SEQ ID NO 140
<211> LENGTH: 20
<212> TYPE: RNA
<213> ORGANISM: Artificial Sequence
<220> FEATURE:
<223> OTHER INFORMATION: guide sequence

<400> SEQUENCE: 140
caucaucuug augucaguuu                                                   20

<210> SEQ ID NO 141
<211> LENGTH: 20
<212> TYPE: RNA
<213> ORGANISM: Artificial Sequence
<220> FEATURE:
<223> OTHER INFORMATION: guide sequence

<400> SEQUENCE: 141
cgaaacugac aucaagauga                                                   20

<210> SEQ ID NO 142
<211> LENGTH: 20
<212> TYPE: RNA
<213> ORGANISM: Artificial Sequence
<220> FEATURE:
<223> OTHER INFORMATION: guide sequence

<400> SEQUENCE: 142
caucaagaug auggagcgag                                                   20

<210> SEQ ID NO 143
<211> LENGTH: 20
<212> TYPE: RNA
<213> ORGANISM: Artificial Sequence
<220> FEATURE:
<223> OTHER INFORMATION: guide sequence

<400> SEQUENCE: 143
caagaugaug gagcgagugg                                                   20

<210> SEQ ID NO 144
<211> LENGTH: 20
<212> TYPE: RNA
<213> ORGANISM: Artificial Sequence
<220> FEATURE:
<223> OTHER INFORMATION: guide sequence

<400> SEQUENCE: 144
cugggauucu cucugguacu                                                   20

<210> SEQ ID NO 145
<211> LENGTH: 20
<212> TYPE: RNA
<213> ORGANISM: Artificial Sequence
```

```
<220> FEATURE:
<223> OTHER INFORMATION: guide sequence

<400> SEQUENCE: 145
ccaguaccag agagaauccc                                              20

<210> SEQ ID NO 146
<211> LENGTH: 20
<212> TYPE: RNA
<213> ORGANISM: Artificial Sequence
<220> FEATURE:
<223> OTHER INFORMATION: guide sequence

<400> SEQUENCE: 146
ccugggauuc ucucgguac                                               20

<210> SEQ ID NO 147
<211> LENGTH: 20
<212> TYPE: RNA
<213> ORGANISM: Artificial Sequence
<220> FEATURE:
<223> OTHER INFORMATION: guide sequence

<400> SEQUENCE: 147
aauaagccug ggauucucuc                                              20

<210> SEQ ID NO 148
<211> LENGTH: 20
<212> TYPE: RNA
<213> ORGANISM: Artificial Sequence
<220> FEATURE:
<223> OTHER INFORMATION: guide sequence

<400> SEQUENCE: 148
ucccaggcuu auuaccaacg                                              20

<210> SEQ ID NO 149
<211> LENGTH: 20
<212> TYPE: RNA
<213> ORGANISM: Artificial Sequence
<220> FEATURE:
<223> OTHER INFORMATION: guide sequence

<400> SEQUENCE: 149
cccaggcuua uuaccaacga                                              20

<210> SEQ ID NO 150
<211> LENGTH: 20
<212> TYPE: RNA
<213> ORGANISM: Artificial Sequence
<220> FEATURE:
<223> OTHER INFORMATION: guide sequence

<400> SEQUENCE: 150
cccucguugg uaauaagccu                                              20

<210> SEQ ID NO 151
<211> LENGTH: 20
<212> TYPE: RNA
<213> ORGANISM: Artificial Sequence
<220> FEATURE:
<223> OTHER INFORMATION: guide sequence

<400> SEQUENCE: 151
aagggcgagg agcuguucac                                              20
```

```
<210> SEQ ID NO 152
<211> LENGTH: 20
<212> TYPE: RNA
<213> ORGANISM: Artificial Sequence
<220> FEATURE:
<223> OTHER INFORMATION: guide sequence

<400> SEQUENCE: 152
agggcgagga gcuguucacc                                               20

<210> SEQ ID NO 153
<211> LENGTH: 20
<212> TYPE: RNA
<213> ORGANISM: Artificial Sequence
<220> FEATURE:
<223> OTHER INFORMATION: guide sequence

<400> SEQUENCE: 153
gggcgaggag cuguucaccg                                               20

<210> SEQ ID NO 154
<211> LENGTH: 20
<212> TYPE: RNA
<213> ORGANISM: Artificial Sequence
<220> FEATURE:
<223> OTHER INFORMATION: guide sequence

<400> SEQUENCE: 154
cgaggagcug uuccaccgggg                                              20

<210> SEQ ID NO 155
<211> LENGTH: 20
<212> TYPE: RNA
<213> ORGANISM: Artificial Sequence
<220> FEATURE:
<223> OTHER INFORMATION: guide sequence

<400> SEQUENCE: 155
caccggggug gugcccaucc                                               20

<210> SEQ ID NO 156
<211> LENGTH: 20
<212> TYPE: RNA
<213> ORGANISM: Artificial Sequence
<220> FEATURE:
<223> OTHER INFORMATION: guide sequence

<400> SEQUENCE: 156
gaccaggaug ggcaccaccc                                               20

<210> SEQ ID NO 157
<211> LENGTH: 20
<212> TYPE: RNA
<213> ORGANISM: Artificial Sequence
<220> FEATURE:
<223> OTHER INFORMATION: guide sequence

<400> SEQUENCE: 157
ggugcccauc cuggucgagc                                               20

<210> SEQ ID NO 158
<211> LENGTH: 20
<212> TYPE: RNA
<213> ORGANISM: Artificial Sequence
<220> FEATURE:
<223> OTHER INFORMATION: guide sequence
```

```
<400> SEQUENCE: 158
cccauccugg ucgagcugga                                              20

<210> SEQ ID NO 159
<211> LENGTH: 20
<212> TYPE: RNA
<213> ORGANISM: Artificial Sequence
<220> FEATURE:
<223> OTHER INFORMATION: guide sequence

<400> SEQUENCE: 159
ccguccagcu cgaccaggau                                              20

<210> SEQ ID NO 160
<211> LENGTH: 20
<212> TYPE: RNA
<213> ORGANISM: Artificial Sequence
<220> FEATURE:
<223> OTHER INFORMATION: guide sequence

<400> SEQUENCE: 160
gccguccagc ucgaccagga                                              20

<210> SEQ ID NO 161
<211> LENGTH: 20
<212> TYPE: RNA
<213> ORGANISM: Artificial Sequence
<220> FEATURE:
<223> OTHER INFORMATION: guide sequence

<400> SEQUENCE: 161
cgucgccguc cagcucgacc                                              20

<210> SEQ ID NO 162
<211> LENGTH: 20
<212> TYPE: RNA
<213> ORGANISM: Artificial Sequence
<220> FEATURE:
<223> OTHER INFORMATION: guide sequence

<400> SEQUENCE: 162
gagcuggacg gcgacgugaa                                              20

<210> SEQ ID NO 163
<211> LENGTH: 20
<212> TYPE: RNA
<213> ORGANISM: Artificial Sequence
<220> FEATURE:
<223> OTHER INFORMATION: guide sequence

<400> SEQUENCE: 163
ggccacaagu ucagcguguc                                              20

<210> SEQ ID NO 164
<211> LENGTH: 20
<212> TYPE: RNA
<213> ORGANISM: Artificial Sequence
<220> FEATURE:
<223> OTHER INFORMATION: guide sequence

<400> SEQUENCE: 164
cgccggacac gcugaacuug                                              20

<210> SEQ ID NO 165
```

```
<211> LENGTH: 20
<212> TYPE: RNA
<213> ORGANISM: Artificial Sequence
<220> FEATURE:
<223> OTHER INFORMATION: guide sequence

<400> SEQUENCE: 165
caaguucagc guguccggcg                                                  20

<210> SEQ ID NO 166
<211> LENGTH: 20
<212> TYPE: RNA
<213> ORGANISM: Artificial Sequence
<220> FEATURE:
<223> OTHER INFORMATION: guide sequence

<400> SEQUENCE: 166
aaguucagcg uguccggcga                                                  20

<210> SEQ ID NO 167
<211> LENGTH: 20
<212> TYPE: RNA
<213> ORGANISM: Artificial Sequence
<220> FEATURE:
<223> OTHER INFORMATION: guide sequence

<400> SEQUENCE: 167
cagcgugucc ggcgagggcg                                                  20

<210> SEQ ID NO 168
<211> LENGTH: 20
<212> TYPE: RNA
<213> ORGANISM: Artificial Sequence
<220> FEATURE:
<223> OTHER INFORMATION: guide sequence

<400> SEQUENCE: 168
agcguguccg gcgagggcga                                                  20

<210> SEQ ID NO 169
<211> LENGTH: 20
<212> TYPE: RNA
<213> ORGANISM: Artificial Sequence
<220> FEATURE:
<223> OTHER INFORMATION: guide sequence

<400> SEQUENCE: 169
ggcaucgccc ucgcccucgc                                                  20

<210> SEQ ID NO 170
<211> LENGTH: 20
<212> TYPE: RNA
<213> ORGANISM: Artificial Sequence
<220> FEATURE:
<223> OTHER INFORMATION: guide sequence

<400> SEQUENCE: 170
ggcgagggcg augccaccua                                                  20

<210> SEQ ID NO 171
<211> LENGTH: 20
<212> TYPE: RNA
<213> ORGANISM: Artificial Sequence
<220> FEATURE:
<223> OTHER INFORMATION: guide sequence

<400> SEQUENCE: 171
```

```
cagggucagc uugccguagg                                                20

<210> SEQ ID NO 172
<211> LENGTH: 20
<212> TYPE: RNA
<213> ORGANISM: Artificial Sequence
<220> FEATURE:
<223> OTHER INFORMATION: guide sequence

<400> SEQUENCE: 172
cuucaggguc agcuugccgu                                                20

<210> SEQ ID NO 173
<211> LENGTH: 20
<212> TYPE: RNA
<213> ORGANISM: Artificial Sequence
<220> FEATURE:
<223> OTHER INFORMATION: guide sequence

<400> SEQUENCE: 173
gguggugcag augaacuuca                                                20

<210> SEQ ID NO 174
<211> LENGTH: 20
<212> TYPE: RNA
<213> ORGANISM: Artificial Sequence
<220> FEATURE:
<223> OTHER INFORMATION: guide sequence

<400> SEQUENCE: 174
cgguggugca gaugaacuuc                                                20

<210> SEQ ID NO 175
<211> LENGTH: 20
<212> TYPE: RNA
<213> ORGANISM: Artificial Sequence
<220> FEATURE:
<223> OTHER INFORMATION: guide sequence

<400> SEQUENCE: 175
cugaaguuca ucugcaccac                                                20

<210> SEQ ID NO 176
<211> LENGTH: 20
<212> TYPE: RNA
<213> ORGANISM: Artificial Sequence
<220> FEATURE:
<223> OTHER INFORMATION: guide sequence

<400> SEQUENCE: 176
gggcacgggc agcuugccgg                                                20

<210> SEQ ID NO 177
<211> LENGTH: 20
<212> TYPE: RNA
<213> ORGANISM: Artificial Sequence
<220> FEATURE:
<223> OTHER INFORMATION: guide sequence

<400> SEQUENCE: 177
ccggcaagcu gcccgugccc                                                20

<210> SEQ ID NO 178
<211> LENGTH: 20
<212> TYPE: RNA
```

```
<213> ORGANISM: Artificial Sequence
<220> FEATURE:
<223> OTHER INFORMATION: guide sequence

<400> SEQUENCE: 178
ccagggcacg ggcagcuugc                                              20

<210> SEQ ID NO 179
<211> LENGTH: 20
<212> TYPE: RNA
<213> ORGANISM: Artificial Sequence
<220> FEATURE:
<223> OTHER INFORMATION: guide sequence

<400> SEQUENCE: 179
acgagggugg gccagggcac                                              20

<210> SEQ ID NO 180
<211> LENGTH: 20
<212> TYPE: RNA
<213> ORGANISM: Artificial Sequence
<220> FEATURE:
<223> OTHER INFORMATION: guide sequence

<400> SEQUENCE: 180
cacgagggug ggccagggca                                              20

<210> SEQ ID NO 181
<211> LENGTH: 20
<212> TYPE: RNA
<213> ORGANISM: Artificial Sequence
<220> FEATURE:
<223> OTHER INFORMATION: guide sequence

<400> SEQUENCE: 181
guggucacga ggugggcca                                               20

<210> SEQ ID NO 182
<211> LENGTH: 20
<212> TYPE: RNA
<213> ORGANISM: Artificial Sequence
<220> FEATURE:
<223> OTHER INFORMATION: guide sequence

<400> SEQUENCE: 182
gguggucacg agggugggcc                                              20

<210> SEQ ID NO 183
<211> LENGTH: 20
<212> TYPE: RNA
<213> ORGANISM: Artificial Sequence
<220> FEATURE:
<223> OTHER INFORMATION: guide sequence

<400> SEQUENCE: 183
gucagggugg ucacgagggu                                              20

<210> SEQ ID NO 184
<211> LENGTH: 20
<212> TYPE: RNA
<213> ORGANISM: Artificial Sequence
<220> FEATURE:
<223> OTHER INFORMATION: guide sequence

<400> SEQUENCE: 184
ggucagggug gucacgaggg                                              20
```

```
<210> SEQ ID NO 185
<211> LENGTH: 20
<212> TYPE: RNA
<213> ORGANISM: Artificial Sequence
<220> FEATURE:
<223> OTHER INFORMATION: guide sequence

<400> SEQUENCE: 185
guaggucagg guggucacga                                              20

<210> SEQ ID NO 186
<211> LENGTH: 20
<212> TYPE: RNA
<213> ORGANISM: Artificial Sequence
<220> FEATURE:
<223> OTHER INFORMATION: guide sequence

<400> SEQUENCE: 186
cguaggucag gguggucacg                                              20

<210> SEQ ID NO 187
<211> LENGTH: 20
<212> TYPE: RNA
<213> ORGANISM: Artificial Sequence
<220> FEATURE:
<223> OTHER INFORMATION: guide sequence

<400> SEQUENCE: 187
cucgugacca cccugaccua                                              20

<210> SEQ ID NO 188
<211> LENGTH: 20
<212> TYPE: RNA
<213> ORGANISM: Artificial Sequence
<220> FEATURE:
<223> OTHER INFORMATION: guide sequence

<400> SEQUENCE: 188
cugcacgccg uaggucaggg                                              20

<210> SEQ ID NO 189
<211> LENGTH: 20
<212> TYPE: RNA
<213> ORGANISM: Artificial Sequence
<220> FEATURE:
<223> OTHER INFORMATION: guide sequence

<400> SEQUENCE: 189
gcacugcacg ccguagguca                                              20

<210> SEQ ID NO 190
<211> LENGTH: 20
<212> TYPE: RNA
<213> ORGANISM: Artificial Sequence
<220> FEATURE:
<223> OTHER INFORMATION: guide sequence

<400> SEQUENCE: 190
agcacugcac gccguagguc                                              20

<210> SEQ ID NO 191
<211> LENGTH: 20
<212> TYPE: RNA
<213> ORGANISM: Artificial Sequence
<220> FEATURE:
```

<223> OTHER INFORMATION: guide sequence

<400> SEQUENCE: 191
gcugaagcac ugcacgccgu                                               20

<210> SEQ ID NO 192
<211> LENGTH: 20
<212> TYPE: RNA
<213> ORGANISM: Artificial Sequence
<220> FEATURE:
<223> OTHER INFORMATION: guide sequence

<400> SEQUENCE: 192
gcuucaugug gucgggguag                                               20

<210> SEQ ID NO 193
<211> LENGTH: 20
<212> TYPE: RNA
<213> ORGANISM: Artificial Sequence
<220> FEATURE:
<223> OTHER INFORMATION: guide sequence

<400> SEQUENCE: 193
cgugcugcuu cauguggucg                                               20

<210> SEQ ID NO 194
<211> LENGTH: 20
<212> TYPE: RNA
<213> ORGANISM: Artificial Sequence
<220> FEATURE:
<223> OTHER INFORMATION: guide sequence

<400> SEQUENCE: 194
ucgugcugcu ucaugugguc                                               20

<210> SEQ ID NO 195
<211> LENGTH: 20
<212> TYPE: RNA
<213> ORGANISM: Artificial Sequence
<220> FEATURE:
<223> OTHER INFORMATION: guide sequence

<400> SEQUENCE: 195
gucgugcugc uucauguggu                                               20

<210> SEQ ID NO 196
<211> LENGTH: 20
<212> TYPE: RNA
<213> ORGANISM: Artificial Sequence
<220> FEATURE:
<223> OTHER INFORMATION: guide sequence

<400> SEQUENCE: 196
agaagucgug cugcuucaug                                               20

<210> SEQ ID NO 197
<211> LENGTH: 20
<212> TYPE: RNA
<213> ORGANISM: Artificial Sequence
<220> FEATURE:
<223> OTHER INFORMATION: guide sequence

<400> SEQUENCE: 197
uucaaguccg ccaugcccga                                               20

```
<210> SEQ ID NO 198
<211> LENGTH: 20
<212> TYPE: RNA
<213> ORGANISM: Artificial Sequence
<220> FEATURE:
<223> OTHER INFORMATION: guide sequence

<400> SEQUENCE: 198
gacguagccu ucgggcaugg                                               20

<210> SEQ ID NO 199
<211> LENGTH: 20
<212> TYPE: RNA
<213> ORGANISM: Artificial Sequence
<220> FEATURE:
<223> OTHER INFORMATION: guide sequence

<400> SEQUENCE: 199
cuggacguag ccuucgggca                                               20

<210> SEQ ID NO 200
<211> LENGTH: 20
<212> TYPE: RNA
<213> ORGANISM: Artificial Sequence
<220> FEATURE:
<223> OTHER INFORMATION: guide sequence

<400> SEQUENCE: 200
caugcccgaa ggcuacgucc                                               20

<210> SEQ ID NO 201
<211> LENGTH: 20
<212> TYPE: RNA
<213> ORGANISM: Artificial Sequence
<220> FEATURE:
<223> OTHER INFORMATION: guide sequence

<400> SEQUENCE: 201
cgcuccugga cguagccuuc                                               20

<210> SEQ ID NO 202
<211> LENGTH: 20
<212> TYPE: RNA
<213> ORGANISM: Artificial Sequence
<220> FEATURE:
<223> OTHER INFORMATION: guide sequence

<400> SEQUENCE: 202
gcgcuccugg acguagccuu                                               20

<210> SEQ ID NO 203
<211> LENGTH: 20
<212> TYPE: RNA
<213> ORGANISM: Artificial Sequence
<220> FEATURE:
<223> OTHER INFORMATION: guide sequence

<400> SEQUENCE: 203
ugaagaagau ggugcgcucc                                               20

<210> SEQ ID NO 204
<211> LENGTH: 20
<212> TYPE: RNA
<213> ORGANISM: Artificial Sequence
<220> FEATURE:
<223> OTHER INFORMATION: guide sequence
```

```
<400> SEQUENCE: 204
ggagcgcacc aucuucuuca                                              20

<210> SEQ ID NO 205
<211> LENGTH: 20
<212> TYPE: RNA
<213> ORGANISM: Artificial Sequence
<220> FEATURE:
<223> OTHER INFORMATION: guide sequence

<400> SEQUENCE: 205
accaucuucu ucaaggacga                                              20

<210> SEQ ID NO 206
<211> LENGTH: 20
<212> TYPE: RNA
<213> ORGANISM: Artificial Sequence
<220> FEATURE:
<223> OTHER INFORMATION: guide sequence

<400> SEQUENCE: 206
gccgucgucc uugaagaaga                                              20

<210> SEQ ID NO 207
<211> LENGTH: 20
<212> TYPE: RNA
<213> ORGANISM: Artificial Sequence
<220> FEATURE:
<223> OTHER INFORMATION: guide sequence

<400> SEQUENCE: 207
caacuacaag acccgcgccg                                              20

<210> SEQ ID NO 208
<211> LENGTH: 20
<212> TYPE: RNA
<213> ORGANISM: Artificial Sequence
<220> FEATURE:
<223> OTHER INFORMATION: guide sequence

<400> SEQUENCE: 208
cucgaacuuc accucggcgc                                              20

<210> SEQ ID NO 209
<211> LENGTH: 20
<212> TYPE: RNA
<213> ORGANISM: Artificial Sequence
<220> FEATURE:
<223> OTHER INFORMATION: guide sequence

<400> SEQUENCE: 209
ccgcgccgag gugaaguucg                                              20

<210> SEQ ID NO 210
<211> LENGTH: 20
<212> TYPE: RNA
<213> ORGANISM: Artificial Sequence
<220> FEATURE:
<223> OTHER INFORMATION: guide sequence

<400> SEQUENCE: 210
ccucgaacuu caccucggcg                                              20

<210> SEQ ID NO 211
<211> LENGTH: 20
```

```
<212> TYPE: RNA
<213> ORGANISM: Artificial Sequence
<220> FEATURE:
<223> OTHER INFORMATION: guide sequence

<400> SEQUENCE: 211
cgcgccgagg ugaaguucga                                               20

<210> SEQ ID NO 212
<211> LENGTH: 20
<212> TYPE: RNA
<213> ORGANISM: Artificial Sequence
<220> FEATURE:
<223> OTHER INFORMATION: guide sequence

<400> SEQUENCE: 212
gucgcccucg aacuucaccu                                               20

<210> SEQ ID NO 213
<211> LENGTH: 20
<212> TYPE: RNA
<213> ORGANISM: Artificial Sequence
<220> FEATURE:
<223> OTHER INFORMATION: guide sequence

<400> SEQUENCE: 213
gaaguucgag ggcgacaccc                                               20

<210> SEQ ID NO 214
<211> LENGTH: 20
<212> TYPE: RNA
<213> ORGANISM: Artificial Sequence
<220> FEATURE:
<223> OTHER INFORMATION: guide sequence

<400> SEQUENCE: 214
cagcucgaug cgguucacca                                               20

<210> SEQ ID NO 215
<211> LENGTH: 20
<212> TYPE: RNA
<213> ORGANISM: Artificial Sequence
<220> FEATURE:
<223> OTHER INFORMATION: guide sequence

<400> SEQUENCE: 215
ucagcucgau gcgguucacc                                               20

<210> SEQ ID NO 216
<211> LENGTH: 20
<212> TYPE: RNA
<213> ORGANISM: Artificial Sequence
<220> FEATURE:
<223> OTHER INFORMATION: guide sequence

<400> SEQUENCE: 216
ggugaaccgc aucgagcuga                                               20

<210> SEQ ID NO 217
<211> LENGTH: 20
<212> TYPE: RNA
<213> ORGANISM: Artificial Sequence
<220> FEATURE:
<223> OTHER INFORMATION: guide sequence

<400> SEQUENCE: 217
```

```
gugaaccgca ucgagcugaa                                               20

<210> SEQ ID NO 218
<211> LENGTH: 20
<212> TYPE: RNA
<213> ORGANISM: Artificial Sequence
<220> FEATURE:
<223> OTHER INFORMATION: guide sequence

<400> SEQUENCE: 218
cgaugcccuu cagcucgaug                                               20

<210> SEQ ID NO 219
<211> LENGTH: 20
<212> TYPE: RNA
<213> ORGANISM: Artificial Sequence
<220> FEATURE:
<223> OTHER INFORMATION: guide sequence

<400> SEQUENCE: 219
gcugaagggc aucgacuuca                                               20

<210> SEQ ID NO 220
<211> LENGTH: 20
<212> TYPE: RNA
<213> ORGANISM: Artificial Sequence
<220> FEATURE:
<223> OTHER INFORMATION: guide sequence

<400> SEQUENCE: 220
gaagggcauc gacuucaagg                                               20

<210> SEQ ID NO 221
<211> LENGTH: 20
<212> TYPE: RNA
<213> ORGANISM: Artificial Sequence
<220> FEATURE:
<223> OTHER INFORMATION: guide sequence

<400> SEQUENCE: 221
ggcaucgacu ucaaggagga                                               20

<210> SEQ ID NO 222
<211> LENGTH: 20
<212> TYPE: RNA
<213> ORGANISM: Artificial Sequence
<220> FEATURE:
<223> OTHER INFORMATION: guide sequence

<400> SEQUENCE: 222
caaggaggac ggcaacaucc                                               20

<210> SEQ ID NO 223
<211> LENGTH: 20
<212> TYPE: RNA
<213> ORGANISM: Artificial Sequence
<220> FEATURE:
<223> OTHER INFORMATION: guide sequence

<400> SEQUENCE: 223
aaggaggacg gcaacauccu                                               20

<210> SEQ ID NO 224
<211> LENGTH: 20
<212> TYPE: RNA
<213> ORGANISM: Artificial Sequence
```

```
<220> FEATURE:
<223> OTHER INFORMATION: guide sequence

<400> SEQUENCE: 224
aggaggacgg caacauccug                                               20

<210> SEQ ID NO 225
<211> LENGTH: 20
<212> TYPE: RNA
<213> ORGANISM: Artificial Sequence
<220> FEATURE:
<223> OTHER INFORMATION: guide sequence

<400> SEQUENCE: 225
caacauccug gggcacaagc                                               20

<210> SEQ ID NO 226
<211> LENGTH: 20
<212> TYPE: RNA
<213> ORGANISM: Artificial Sequence
<220> FEATURE:
<223> OTHER INFORMATION: guide sequence

<400> SEQUENCE: 226
uguacuccag cuugugcccc                                               20

<210> SEQ ID NO 227
<211> LENGTH: 20
<212> TYPE: RNA
<213> ORGANISM: Artificial Sequence
<220> FEATURE:
<223> OTHER INFORMATION: guide sequence

<400> SEQUENCE: 227
cagccacaac gucuauauca                                               20

<210> SEQ ID NO 228
<211> LENGTH: 20
<212> TYPE: RNA
<213> ORGANISM: Artificial Sequence
<220> FEATURE:
<223> OTHER INFORMATION: guide sequence

<400> SEQUENCE: 228
cggccaugau auagacguug                                               20

<210> SEQ ID NO 229
<211> LENGTH: 20
<212> TYPE: RNA
<213> ORGANISM: Artificial Sequence
<220> FEATURE:
<223> OTHER INFORMATION: guide sequence

<400> SEQUENCE: 229
auggccgaca agcagaagaa                                               20

<210> SEQ ID NO 230
<211> LENGTH: 20
<212> TYPE: RNA
<213> ORGANISM: Artificial Sequence
<220> FEATURE:
<223> OTHER INFORMATION: guide sequence

<400> SEQUENCE: 230
gaugccguuc uucugcuugu                                               20
```

<210> SEQ ID NO 231
<211> LENGTH: 20
<212> TYPE: RNA
<213> ORGANISM: Artificial Sequence
<220> FEATURE:
<223> OTHER INFORMATION: guide sequence

<400> SEQUENCE: 231
caagcagaag aacggcauca                                               20

<210> SEQ ID NO 232
<211> LENGTH: 20
<212> TYPE: RNA
<213> ORGANISM: Artificial Sequence
<220> FEATURE:
<223> OTHER INFORMATION: guide sequence

<400> SEQUENCE: 232
caagauccgc cacaacaucg                                               20

<210> SEQ ID NO 233
<211> LENGTH: 20
<212> TYPE: RNA
<213> ORGANISM: Artificial Sequence
<220> FEATURE:
<223> OTHER INFORMATION: guide sequence

<400> SEQUENCE: 233
auccgccaca acaucgagga                                               20

<210> SEQ ID NO 234
<211> LENGTH: 20
<212> TYPE: RNA
<213> ORGANISM: Artificial Sequence
<220> FEATURE:
<223> OTHER INFORMATION: guide sequence

<400> SEQUENCE: 234
ugccguccuc gauguugugg                                               20

<210> SEQ ID NO 235
<211> LENGTH: 20
<212> TYPE: RNA
<213> ORGANISM: Artificial Sequence
<220> FEATURE:
<223> OTHER INFORMATION: guide sequence

<400> SEQUENCE: 235
cgcugccguc cucgauguug                                               20

<210> SEQ ID NO 236
<211> LENGTH: 20
<212> TYPE: RNA
<213> ORGANISM: Artificial Sequence
<220> FEATURE:
<223> OTHER INFORMATION: guide sequence

<400> SEQUENCE: 236
gguguucugc ugguaguggu                                               20

<210> SEQ ID NO 237
<211> LENGTH: 20
<212> TYPE: RNA
<213> ORGANISM: Artificial Sequence
<220> FEATURE:
<223> OTHER INFORMATION: guide sequence

```
<400> SEQUENCE: 237
uggggguguu cugcuggaug                                           20

<210> SEQ ID NO 238
<211> LENGTH: 20
<212> TYPE: RNA
<213> ORGANISM: Artificial Sequence
<220> FEATURE:
<223> OTHER INFORMATION: guide sequence

<400> SEQUENCE: 238
uaccagcaga acaccccccau                                          20

<210> SEQ ID NO 239
<211> LENGTH: 20
<212> TYPE: RNA
<213> ORGANISM: Artificial Sequence
<220> FEATURE:
<223> OTHER INFORMATION: guide sequence

<400> SEQUENCE: 239
cgccgauggg gguguucugc                                           20

<210> SEQ ID NO 240
<211> LENGTH: 20
<212> TYPE: RNA
<213> ORGANISM: Artificial Sequence
<220> FEATURE:
<223> OTHER INFORMATION: guide sequence

<400> SEQUENCE: 240
cagaacaccc ccaucggcga                                           20

<210> SEQ ID NO 241
<211> LENGTH: 20
<212> TYPE: RNA
<213> ORGANISM: Artificial Sequence
<220> FEATURE:
<223> OTHER INFORMATION: guide sequence

<400> SEQUENCE: 241
cacggggccg ucgccgaugg                                           20

<210> SEQ ID NO 242
<211> LENGTH: 20
<212> TYPE: RNA
<213> ORGANISM: Artificial Sequence
<220> FEATURE:
<223> OTHER INFORMATION: guide sequence

<400> SEQUENCE: 242
gcacggggcc gucgccgaug                                           20

<210> SEQ ID NO 243
<211> LENGTH: 20
<212> TYPE: RNA
<213> ORGANISM: Artificial Sequence
<220> FEATURE:
<223> OTHER INFORMATION: guide sequence

<400> SEQUENCE: 243
agcacggggc cgucgccgau                                           20

<210> SEQ ID NO 244
```

<211> LENGTH: 20
<212> TYPE: RNA
<213> ORGANISM: Artificial Sequence
<220> FEATURE:
<223> OTHER INFORMATION: guide sequence

<400> SEQUENCE: 244
cagcacgggg ccgucgccga                                               20

<210> SEQ ID NO 245
<211> LENGTH: 20
<212> TYPE: RNA
<213> ORGANISM: Artificial Sequence
<220> FEATURE:
<223> OTHER INFORMATION: guide sequence

<400> SEQUENCE: 245
gguugucggg cagcagcacg                                               20

<210> SEQ ID NO 246
<211> LENGTH: 20
<212> TYPE: RNA
<213> ORGANISM: Artificial Sequence
<220> FEATURE:
<223> OTHER INFORMATION: guide sequence

<400> SEQUENCE: 246
ugguugucgg gcagcagcac                                               20

<210> SEQ ID NO 247
<211> LENGTH: 20
<212> TYPE: RNA
<213> ORGANISM: Artificial Sequence
<220> FEATURE:
<223> OTHER INFORMATION: guide sequence

<400> SEQUENCE: 247
gugguugucg ggcagcagca                                               20

<210> SEQ ID NO 248
<211> LENGTH: 20
<212> TYPE: RNA
<213> ORGANISM: Artificial Sequence
<220> FEATURE:
<223> OTHER INFORMATION: guide sequence

<400> SEQUENCE: 248
gugcucaggu aguggruuguc                                              20

<210> SEQ ID NO 249
<211> LENGTH: 20
<212> TYPE: RNA
<213> ORGANISM: Artificial Sequence
<220> FEATURE:
<223> OTHER INFORMATION: guide sequence

<400> SEQUENCE: 249
ggugcucagg uagugguugu                                               20

<210> SEQ ID NO 250
<211> LENGTH: 20
<212> TYPE: RNA
<213> ORGANISM: Artificial Sequence
<220> FEATURE:
<223> OTHER INFORMATION: guide sequence

<400> SEQUENCE: 250
cggacugggu gcucagguag                                              20

<210> SEQ ID NO 251
<211> LENGTH: 20
<212> TYPE: RNA
<213> ORGANISM: Artificial Sequence
<220> FEATURE:
<223> OTHER INFORMATION: guide sequence

<400> SEQUENCE: 251
ucagggcgga cugggugcuc                                              20

<210> SEQ ID NO 252
<211> LENGTH: 20
<212> TYPE: RNA
<213> ORGANISM: Artificial Sequence
<220> FEATURE:
<223> OTHER INFORMATION: guide sequence

<400> SEQUENCE: 252
gucuuugcuc agggcggacu                                              20

<210> SEQ ID NO 253
<211> LENGTH: 20
<212> TYPE: RNA
<213> ORGANISM: Artificial Sequence
<220> FEATURE:
<223> OTHER INFORMATION: guide sequence

<400> SEQUENCE: 253
ggucuuugcu cagggcggac                                              20

<210> SEQ ID NO 254
<211> LENGTH: 20
<212> TYPE: RNA
<213> ORGANISM: Artificial Sequence
<220> FEATURE:
<223> OTHER INFORMATION: guide sequence

<400> SEQUENCE: 254
guuggggucu uugcucaggg                                              20

<210> SEQ ID NO 255
<211> LENGTH: 20
<212> TYPE: RNA
<213> ORGANISM: Artificial Sequence
<220> FEATURE:
<223> OTHER INFORMATION: guide sequence

<400> SEQUENCE: 255
cucguugggg ucuuugcuca                                              20

<210> SEQ ID NO 256
<211> LENGTH: 20
<212> TYPE: RNA
<213> ORGANISM: Artificial Sequence
<220> FEATURE:
<223> OTHER INFORMATION: guide sequence

<400> SEQUENCE: 256
ucucguuggg gucuuugcuc                                              20

<210> SEQ ID NO 257
<211> LENGTH: 20
<212> TYPE: RNA

```
<213> ORGANISM: Artificial Sequence
<220> FEATURE:
<223> OTHER INFORMATION: guide sequence

<400> SEQUENCE: 257
ugugaucgcg cuucucguug                                               20

<210> SEQ ID NO 258
<211> LENGTH: 20
<212> TYPE: RNA
<213> ORGANISM: Artificial Sequence
<220> FEATURE:
<223> OTHER INFORMATION: guide sequence

<400> SEQUENCE: 258
augugaucgc gcuucucguu                                               20

<210> SEQ ID NO 259
<211> LENGTH: 20
<212> TYPE: RNA
<213> ORGANISM: Artificial Sequence
<220> FEATURE:
<223> OTHER INFORMATION: guide sequence

<400> SEQUENCE: 259
caugugaucg cgcuucucgu                                               20

<210> SEQ ID NO 260
<211> LENGTH: 20
<212> TYPE: RNA
<213> ORGANISM: Artificial Sequence
<220> FEATURE:
<223> OTHER INFORMATION: guide sequence

<400> SEQUENCE: 260
caacgagaag cgcgaucaca                                               20

<210> SEQ ID NO 261
<211> LENGTH: 20
<212> TYPE: RNA
<213> ORGANISM: Artificial Sequence
<220> FEATURE:
<223> OTHER INFORMATION: guide sequence

<400> SEQUENCE: 261
gcgcgaucac augguccugc                                               20

<210> SEQ ID NO 262
<211> LENGTH: 20
<212> TYPE: RNA
<213> ORGANISM: Artificial Sequence
<220> FEATURE:
<223> OTHER INFORMATION: guide sequence

<400> SEQUENCE: 262
cggcggucac gaacuccagc                                               20

<210> SEQ ID NO 263
<211> LENGTH: 20
<212> TYPE: RNA
<213> ORGANISM: Artificial Sequence
<220> FEATURE:
<223> OTHER INFORMATION: guide sequence

<400> SEQUENCE: 263
cuggaguucg ugaccgccgc                                               20
```

<210> SEQ ID NO 264
<211> LENGTH: 20
<212> TYPE: RNA
<213> ORGANISM: Artificial Sequence
<220> FEATURE:
<223> OTHER INFORMATION: guide sequence

<400> SEQUENCE: 264
uggaguucgu gaccgccgcc                                                    20

<210> SEQ ID NO 265
<211> LENGTH: 20
<212> TYPE: RNA
<213> ORGANISM: Artificial Sequence
<220> FEATURE:
<223> OTHER INFORMATION: guide sequence

<400> SEQUENCE: 265
accgccgccg ggaucacuca                                                    20

<210> SEQ ID NO 266
<211> LENGTH: 20
<212> TYPE: RNA
<213> ORGANISM: Artificial Sequence
<220> FEATURE:
<223> OTHER INFORMATION: guide sequence

<400> SEQUENCE: 266
gccgugagug aucccggcgg                                                    20

<210> SEQ ID NO 267
<211> LENGTH: 20
<212> TYPE: RNA
<213> ORGANISM: Artificial Sequence
<220> FEATURE:
<223> OTHER INFORMATION: guide sequence

<400> SEQUENCE: 267
caugccguga gugaucccgg                                                    20

<210> SEQ ID NO 268
<211> LENGTH: 20
<212> TYPE: RNA
<213> ORGANISM: Artificial Sequence
<220> FEATURE:
<223> OTHER INFORMATION: guide sequence

<400> SEQUENCE: 268
cgccgggauc acucacggca                                                    20

<210> SEQ ID NO 269
<211> LENGTH: 20
<212> TYPE: RNA
<213> ORGANISM: Artificial Sequence
<220> FEATURE:
<223> OTHER INFORMATION: guide sequence

<400> SEQUENCE: 269
guccaugccg ugagugaucc                                                    20

<210> SEQ ID NO 270
<211> LENGTH: 12
<212> TYPE: RNA
<213> ORGANISM: Streptococcus pyogenes

```
<400> SEQUENCE: 270
guuuuagagc ua                                                          12

<210> SEQ ID NO 271
<211> LENGTH: 13
<212> TYPE: RNA
<213> ORGANISM: Campylobacter jejuni

<400> SEQUENCE: 271
guuuuagucc cuu                                                         13

<210> SEQ ID NO 272
<211> LENGTH: 13
<212> TYPE: RNA
<213> ORGANISM: Campylobacter jejuni

<400> SEQUENCE: 272
guuuuagucc cuu                                                         13

<210> SEQ ID NO 273
<211> LENGTH: 14
<212> TYPE: RNA
<213> ORGANISM: Streptococcus pyogenes

<400> SEQUENCE: 273
uagcaaguua aaau                                                        14

<210> SEQ ID NO 274
<211> LENGTH: 25
<212> TYPE: RNA
<213> ORGANISM: Campylobacter jejuni

<400> SEQUENCE: 274
aagaaauuua aaagggacu aaaau                                             25

<210> SEQ ID NO 275
<211> LENGTH: 13
<212> TYPE: RNA
<213> ORGANISM: Campylobacter jejuni

<400> SEQUENCE: 275
aagggacuaa aau                                                         13

<210> SEQ ID NO 276
<211> LENGTH: 34
<212> TYPE: RNA
<213> ORGANISM: Streptococcus pyogenes

<400> SEQUENCE: 276
uuaucaacuu gaaaaagugg caccgagucg gugc                                  34

<210> SEQ ID NO 277
<211> LENGTH: 38
<212> TYPE: RNA
<213> ORGANISM: Campylobacter jejuni

<400> SEQUENCE: 277
gggacucugc gggguuacaa ucccuaaaa ccgcuuuu                               38

<210> SEQ ID NO 278
<211> LENGTH: 20
<212> TYPE: DNA
<213> ORGANISM: Artificial Sequence
```

```
<220> FEATURE:
<223> OTHER INFORMATION: PRNP forward primer

<400> SEQUENCE: 278
gaggtgttcg ttcgtttttc                                            20

<210> SEQ ID NO 279
<211> LENGTH: 20
<212> TYPE: DNA
<213> ORGANISM: Artificial Sequence
<220> FEATURE:
<223> OTHER INFORMATION: PRNP reverse primer

<400> SEQUENCE: 279
ctaccagttt cctgtgctta                                            20

<210> SEQ ID NO 280
<211> LENGTH: 20
<212> TYPE: DNA
<213> ORGANISM: Artificial Sequence
<220> FEATURE:
<223> OTHER INFORMATION: BLG forward primer

<400> SEQUENCE: 280
cttgtctaag aggctgaccc                                            20

<210> SEQ ID NO 281
<211> LENGTH: 20
<212> TYPE: DNA
<213> ORGANISM: Artificial Sequence
<220> FEATURE:
<223> OTHER INFORMATION: BLG reverse primer

<400> SEQUENCE: 281
gagaagatgg ctgtctgctc                                            20

<210> SEQ ID NO 282
<211> LENGTH: 20
<212> TYPE: DNA
<213> ORGANISM: Artificial Sequence
<220> FEATURE:
<223> OTHER INFORMATION: DNA sequence for obtaining GFP sgRNA

<400> SEQUENCE: 282
cctcgagctg gacggcgacg                                            20

<210> SEQ ID NO 283
<211> LENGTH: 79
<212> TYPE: DNA
<213> ORGANISM: Artificial Sequence
<220> FEATURE:
<223> OTHER INFORMATION: DNA sequence for knock-in

<400> SEQUENCE: 283
ataacttcgt ataatgtatg ctatacgaag ttatcacgat cgacgataac ttcgtatagg   60
atactttata cgaagttat                                              79

<210> SEQ ID NO 284
<211> LENGTH: 19
<212> TYPE: DNA
<213> ORGANISM: Artificial Sequence
<220> FEATURE:
<223> OTHER INFORMATION: GFP forward primer

<400> SEQUENCE: 284
```

```
gctctagagc ctctgctaa                                                    19

<210> SEQ ID NO 285
<211> LENGTH: 21
<212> TYPE: DNA
<213> ORGANISM: Artificial Sequence
<220> FEATURE:
<223> OTHER INFORMATION: GFP reverse primer

<400> SEQUENCE: 285
cacatgaagc agcacgactt c                                                 21
```

METHOD AND COMPOSITION FOR SORTING OUT OF CELL COMPRISING A MODIFIED GENE

CROSS-REFERENCE TO RELATED APPLICATIONS

This application claims priority to Korean Patent Application No. 10-2021-0000494, filed on 4 Jan. 2021. The entire disclosure of the application identified in this paragraph are incorporated herein by reference.

TECHNICAL FIELD

Sorting Out Genetically Modified Cells

The present disclosure relates to a method for sorting out genetically modified cells. Recently, research for producing genetically modified cells or animals through modification of inserting or removing a gene having a specific trait has been conducted. In the above research, in order to confirm whether the cell has been genetically modified or to use the genetically modified cell, a process for checking whether the cell is genetically modified is essential.

An embodiment of the present disclosure relates to a method for more efficiently sorting out genetically modified cells in the genetic modification study.

BACKGROUND

Genetic modification technology is widely used for the treatment of genetic diseases and incurable diseases and the improvement of animal and plant varieties. In this case, genetic modification means inserting, deleting, or substituting a specific DNA in the genome of an organism.

Recently, widely used genetic modification technologies include Zinc Finger Nucleases (ZFNs), Transcription Activator-Like Effector Nucleases (TALENs), and the CRISPR/Cas system. The current genetic modification-related market is expected to expand from $3.62 billion (about KRW 4.86 trillion) in 2018 to $7.12 billion (about KRW 8.37 trillion) in 2023, growing at an average annual rate of 14.5%, of which CRISPR/Cas9 technology is the largest market size with $1.95 billion (53.8% occupied) in 2018 (Biotechnology Policy Research Center, Global Genome Editing Technologies Industry Outlook (Frost & Sullivan Analysis), 2019.3).

In the above genetic modification technology, after modifying a specific DNA in the genome of an organism, it is essential to check whether the specific DNA has been modified or not. That is, the process of sorting out genetically modified cells is essential. Conventionally, PCR has been widely used as a method for checking whether genes have been modified. However, the method of confirming the insertion, deletion, or substitution of a specific DNA through PCR was inefficient in that cells were consumed in this process, or an additional analysis step and time were required.

RELATED ART LITERATURE

Patent Literature

U.S. Ser. No. 16/612,142

SUMMARY

Technical Problem

Conventionally, in order to sort out genetically modified cells, a process of analyzing the cells was required. That is, in addition to the step of transforming cells or animals according to the genetic modification method, an additional step of checking whether the genetic modification was performed or not was required.

In this way, in order to select genetically modified cells, an additional analysis whether genes are genetically modified is inefficient in the cell sorting out process. In addition, since cells that have undergone the analysis step cannot be utilized, there is a problem that cells are consumed.

Accordingly, an objective of the present disclosure is to provide a more efficient method for sorting out genetically modified cells.

Technical Solution

The present disclosure provides a method for sorting out a cell comprising a modified gene on a target locus in the genome.

According to an embodiment of the present disclosure, the method comprises: preparing fluorescent bovine cells (bovine cells exhibiting fluorescence); treating the fluorescent bovine cells with a composition; and selecting non-fluorescent bovine cells (bovine cells that do not exhibit fluorescence).

In this case, the fluorescent bovine cell includes a fluorescent protein gene on one or more positions in a genome, wherein the fluorescent protein gene is a different gene from a gene on the target locus in the genome, and the composition comprises: a guide RNA for the fluorescent protein gene or a nucleic acid encoding the same; a guide RNA for the gene on the target locus in the genome or a nucleic acid encoding the same; and a Cas protein or a nucleic acid encoding the same, wherein the non-fluorescent bovine cell comprises a modified gene on the target locus in the genome.

In this case, in the method, the composition further comprises a transgene to be inserted into the target locus in the genome.

In this time, in the method, the step of preparing the fluorescent bovine cells comprises to use a cow comprising the fluorescent protein gene located on 95433564-95434563 position of chromosome 4; 113823097-113823101 position of chromosome 4; and 20085913-20086912 position of chromosome 6 in a genome.

In this case, in the step of treating the composition on the fluorescent bovine cell in the method, the guide RNA for the fluorescent protein gene or the nucleic acid encoding the same, and the guide RNA for the gene on the target locus in a genome or the nucleic acid encoding the same are simultaneously treated.

In this case, in the step of treating the fluorescent bovine cells with the composition in the method, the composition is treated in a vector form.

In this case, in the step of treating the fluorescent bovine cells with the composition in the method, the composition is treated in a ribonucleoprotein (RNP) form.

The present disclosure provides a cell including a modified gene on a target locus in the genome.

As an embodiment of the present disclosure, the cell is a bovine cell, the bovine cell includes a modified gene on a target locus in a genome and a modified fluorescent protein gene on one or more positions in the genome, wherein the fluorescent protein gene is a different gene from the gene on the target locus in the genome.

In this case, the modified gene in the bovine cell is a beta-lactoglobulin (BLG) gene or a prion (PRNP) gene.

In this case, the bovine cell includes the modified fluorescent protein gene on three positions in the genome.

In this case, the one or more positions in the genome include at least one of 95433564-95434563 position of chromosome 4; 113823097-113823101 position of chromosome 4; and 20085913-20086912 position of chromosome 6.

The present disclosure provides a method for producing an animal including a modified gene on a target locus in the genome.

As an embodiment of the present disclosure, the animal is a cow, and the method includes: preparing a cell that expresses fluorescence; treating composition to the cell that expresses fluorescence; selecting a non-fluorescent cell; and transplanting the non-fluorescent cell into the uterus of a surrogate mother.

In this case, the cell includes a fluorescent protein gene on one or more positions in a genome, the fluorescent protein gene is a different gene from a gene on the target locus in a genome, and the composition includes a guide RNA for the fluorescent protein gene or a nucleic acid encoding the same; a guide RNA for the gene on the target locus in the genome or a nucleic acid encoding the same; and a Cas protein or a nucleic acid encoding the same, wherein the non-fluorescent cell includes a modified gene on the target locus in a genome.

In this case, the modified gene is a beta-lactoglobulin (BLG) gene or a prion (PRNP) gene.

In this case, the composition further includes a transgene to be inserted on the target locus in the genome.

In this case, the one or more positions in the genome include at least one of 95433564-95434563 positions of chromosome 4; 113823097-113823101 positions of chromosome 4; and 20085913-20086912 positions of chromosome 6.

The present disclosure provides an animal including a modified gene on a target locus in the genome.

As an embodiment of the present disclosure, the animal is a cow, the cow includes a modified gene on a target locus in a genome, the cow includes a modified fluorescent protein gene on one or more positions in the genome, and the fluorescent protein gene is a different gene from the gene on the target locus gene in the genome, and the fluorescent protein gene present in the genome is transferred the same site in a next generation.

In this case, the modified gene in the cow is a beta-lactoglobulin gene or a prion (PRNP) gene.

In this case, the cow comprises a fluorescent protein gene modified on three positions in the genome.

In this case, the one or more positions in the genome comprise at least one of 95433564-95434563 positions of chromosome 4; 113823097-113823101 positions of chromosome 4; and 20085913-20086912 positions of chromosome 6.

The present disclosure provides a kit for sorting out cells including a modified gene on a target locus in the genome.

As an embodiment of the present disclosure, the kit comprises: a fluorescent bovine cell; a guide RNA for a fluorescent protein gene, or a nucleic acid encoding the same; and a Cas protein, or a nucleic acid encoding the same, wherein the fluorescent bovine cell includes a fluorescent protein gene on one or more positions in a genome.

In this case, the fluorescent protein in the kit is a green fluorescent protein.

In this case, the kit further comprises a guide RNA for a gene on a target locus in the genome or a nucleic acid encoding the same.

In this case, the kit further includes a transgene to be inserted on the target locus in the genome, in addition to the guide RNA for a gene on a target locus gene in the genome or a nucleic acid encoding the same.

In this case, the Cas protein in the kit is a Cas9 protein or a Cpf1 protein.

In this case, in the kit, the fluorescent bovine cell includes a fluorescent protein gene on three positions in the genome.

In this case, the one or more positions in the genome include at least one of 95433564-95434563 position of chromosome 4; 113823097-113823101 position of chromosome 4; and 20085913-20086912 position of chromosome 6.

Advantageous Effects of Invention

The methods and materials for sorting out genetically modified cells disclosed herein provide a more efficient method of sorting out cells.

1) Since an additional analysis process for sorting out genetically modified cells is not required, it is possible to prevent cell consumption during the analysis process.

2) Since an additional analysis process for sorting out genetically modified cells is not required, the time and effort required for the analysis process may be saved.

3, 4, 5, 8, 9, 10, 19, 21, 22, 24, 25 in (a); 3, 4, 5, 6, 7, 8, 9, 10, 11 in (b) represent mutant colonies, M represents a marker, NC represents a negative control group, and PC represents a positive control group.

Figure 1:
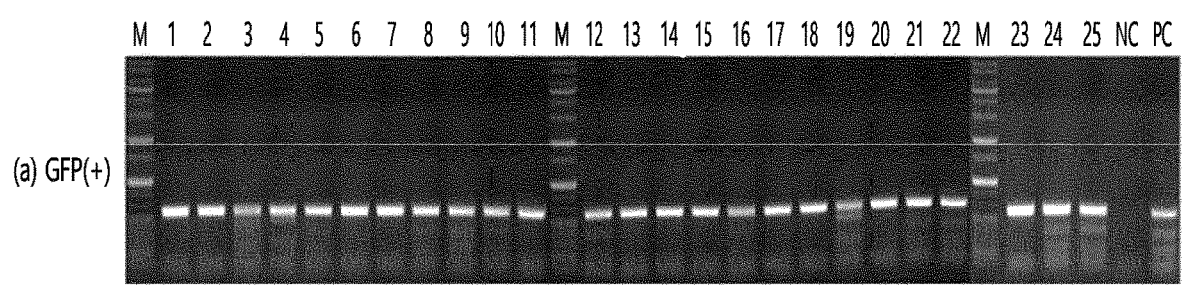
FIG. 1 shows a mutation test result of a prion (PRNP) gene in a single cell colony.
Figure 1:
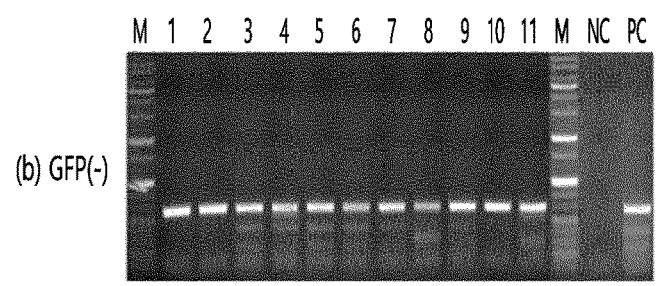
Figure 2:
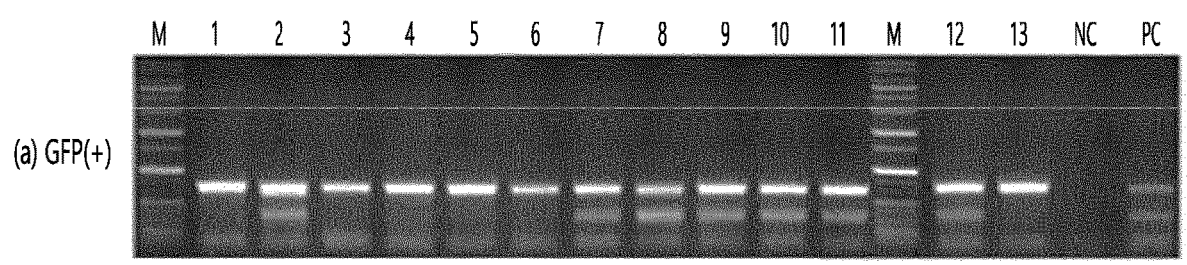
Figure 2:
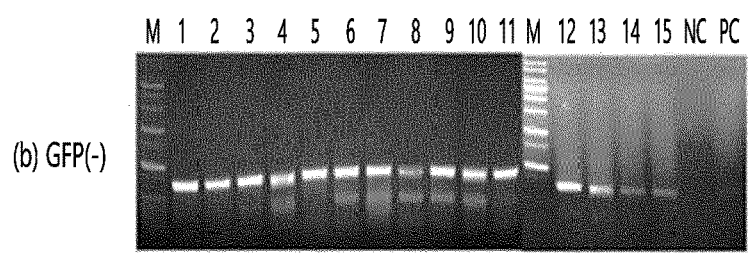

FIG. 2 shows a mutation test result of the beta-lactoglobulin (BLG) gene in a single cell colony.

2, 7, 8, 9, 10, 11, 12 in (a); 3, 4, 6, 7, 8, 9, 10, 11, 12, 13, 14 in (b) represent mutant colonies, M represents a marker, NC represents a negative control group, and PC represents a positive control group.

Figure 3:
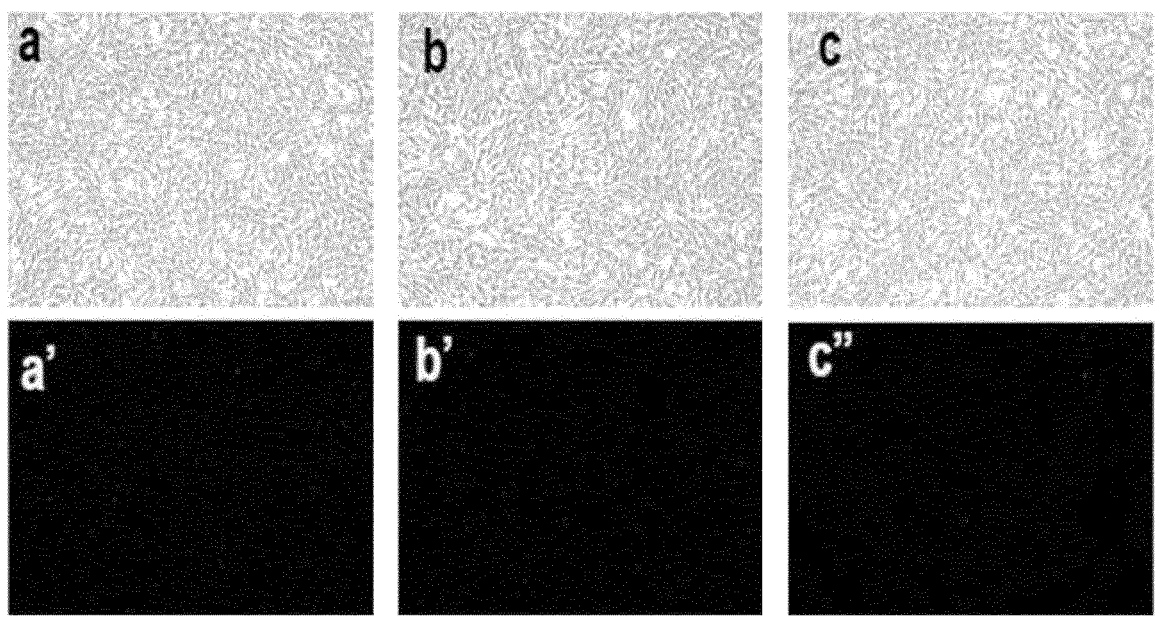

FIG. 3 is a photograph of cells.

a) Bright-field image and a') fluorescence image of early passage cultured cells; b) bright-field images and b') fluorescence images of primary cells transfected with Cas9 and sgRNA for GFP; c) bright-field images and c') fluorescence images of primary cells transfected with Cas9 and sgRNA for GFP and PRNP.

Figure 4:
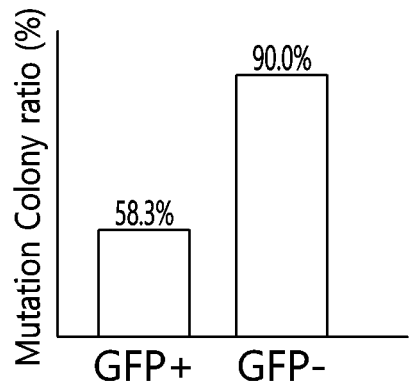
Figure 4:
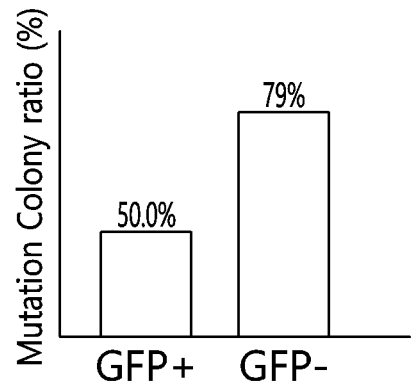

FIG. 4 shows a result showing the ratio of (a) prion (PRNP) gene knock-out cell ratio and (b) beta-lactoglobulin (BLG) gene knock-out cell ratio in GFP (+) cells and GFP (−) cells. The mutant colony ratio of the prion (PRNP) gene in the GFP negative cell group was higher (90.0% vs. 58.3%) than in the GFP positive cell group. The mutant colony ratio of beta-lactoglobulin (BLG) genes in the GFP negative cell group was higher (79% vs. 58%) than in the GFP positive cell group.

Figure 5:
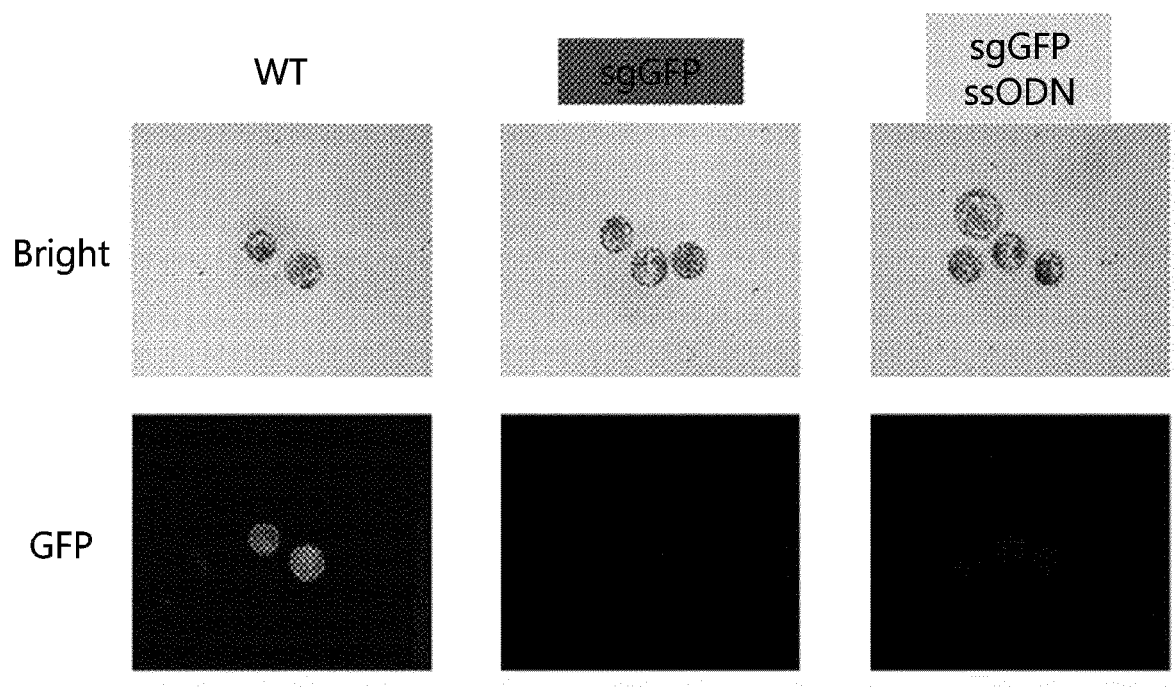

FIG. 5 is a photomicrograph of a group of GFP-expressing bovine cells (control group), a group in which GFP-expressing bovine cells were treated with GFP sgRNA and Cas9 protein (knock-out group), and a group in which GFP-expressing bovine cells were treated with GFP sgRNA, Cas9 protein, and Donor DNA (knock-in group).

Figure 6:
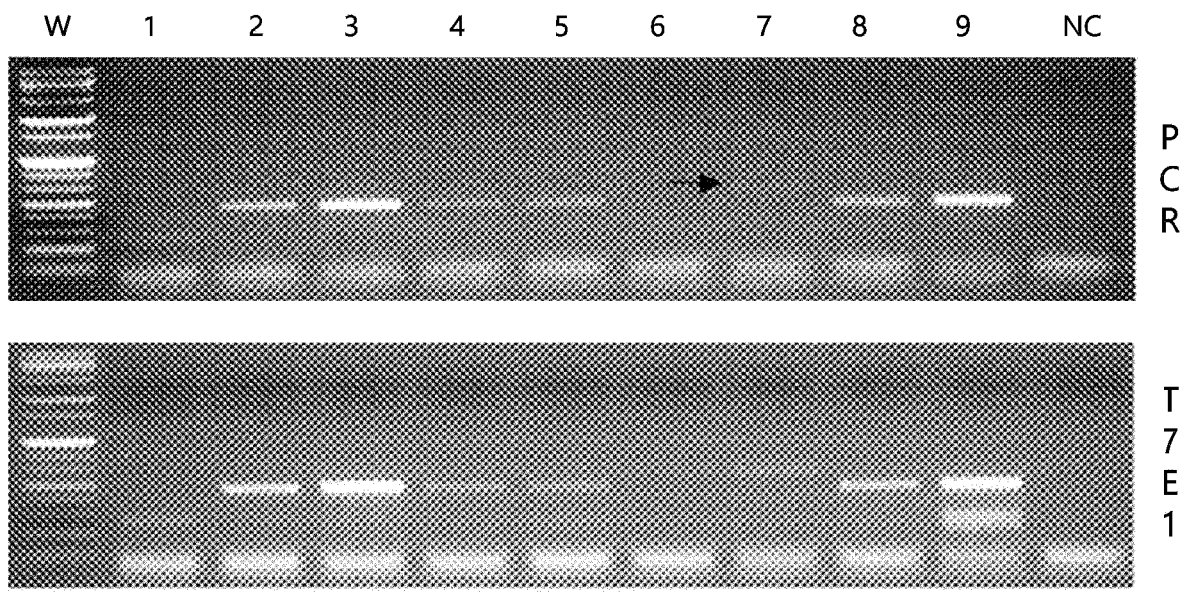

FIG. 6 is a PCR test result for confirming the GFP gene extracted from blastocysts of the obtained three groups and the gene inserted into the GFP gene sequence.

DETAILED DESCRIPTION

Term Definition

Definitions of key terms used in this specification are as follows.

Gene Modification or Gene Editing

Genetic modification or genetic manipulation, as used herein, refers to the creation of an insertion, deletion and/or substitution of a specific DNA sequence on a target locus in the genome of a cell. The genetic modification includes a gene mutation. The genetic modification includes a gene knock-out of a target locus in the genome and/or a knock-in of a transgene. The gene knock-out refers to a modification that reduces the function of a gene so that the expression of the gene is undetectably small or not expressed. The gene knock-in refers to a modification of inserting a gene to be expressed in a cell. In this case, in the present disclosure, the genetically modified or genetically edited cell may be referred to as an 'engineered cell'.

Safe Harbor

Safe harbor, as used herein, means a specific position in the genome where an inserted gene can be stably expressed in the cell without interfering with the expression or regulation of the gene adjacent to the inserted position after a specific gene is inserted into the genome of a cell.

Target Locus (Target Region)

As used herein, a 'target locus' or a 'target region' refers to a region on a genome in which a gene to be edited exists. That is, it means including a region to be artificially manipulated on the genome and is a region including the protospacer sequence and the target sequence indicated below.

Gene on a Target Locus

As used herein, a gene on a target locus means a gene located at a specific target locus (target region) in a genome, and the gene is a gene in which cleavage occurs by gene editing. As an example, the gene may be knocked out through cleavage. As another example, after the gene is cleavage, a transgene may be inserted on the cleavage site.

Protospacer Sequence

The term 'protospacer sequence' refers to about 20 sequences adjacent to the PAM sequence in the target region of the present application. The protospacer sequence and the target sequence are complementary sequences. That is, it means the same sequence as the guide sequence that complementarily binds to the target sequence. However, the guide sequence may have the same sequence in which T (thymine) of the protospacer sequence is substituted with U (uracil).

Target Sequence

The term 'target sequence' of the present application is a sequence included in the target region of the present application, and is a sequence complementary binding to a protospacer sequence. The target sequence may bind complementary to the guide sequence.

Meaning of A, T, C, G, and U

As used herein, the symbols A, T, C, G, and U are interpreted as meanings understood by those of ordinary skilled in the art. It may be properly interpreted as a base, a nucleoside, or a nucleotide on DNA or RNA according to context and technology. For example, when it means a base, it can be interpreted as adenine (A), thymine (T), cytosine (C), guanine (G) or uracil (U) itself, respectively. When it means a nucleoside, it can be interpreted as adenosine (A), thymine (T), cytidine (C), guanosine (G), or uridine (U), respectively, and when it means a nucleotide in the sequence, it should be interpreted to mean a nucleotide including each of the nucleosides.

CRISPR(Clustered Regularly Interspaced Short Palindromic Repeats)-Cas System

The CRISPR-Cas system means that it is derived from an acquired immune system that stores genetic information of pathogens that have invaded from the outside in bacteria and cuts them when re-invading later.

The CRISPR Cas system used herein is composed of a guide RNA capable of recognizing a specific DNA sequence and a Cas protein capable of cutting DNA. The guide RNA may interact with the Cas protein. The guide RNA may form a guide RNA-Cas protein complex through this interaction with the Cas protein. The guide RNA-Cas protein complex guides the Cas protein to a specific region of DNA, allowing DNA cleavage to occur in that region.

DNA cleavage caused by the CRISPR-Cas system is repaired by homology directed repair (HDR) or non-homologous end joining in cells. In homologous recombination, when template DNA of a homologous base sequence exists, repair occurs based on the homologous template DNA. On the other hand, in non-homologous end joining, DNA repair occurs when several bases are inserted or deleted (indels, insertions, or deletions) in the process of joining the cut ends.

The CRISPR-Cas system may be used for gene editing through DNA cleavage.

Guide RNA

Guide RNA, as used herein, refers to an RNA that recognizes a partial nucleotide sequence of DNA in a cell and interacts with a Cas protein.

The guide RNA includes crRNA and/or tracrRNA.

As an example, the guide RNA may be composed of only crRNA, and in another example, the guide RNA may be composed of crRNA and tracrRNA.

The guide RNA may be a single guide RNA in which the crRNA and the tracrRNA are composed of a single strand, or a dual guide RNA in which the crRNA and the tracrRNA are composed of two strand separated from each other.

crRNA

The crRNA comprises a guide sequence and may further comprise a first complementary sequence complementary binding to the tracrRNA.

The guide sequence is a sequence in which a sequence complementary to a target sequence has the same identity as a protospacer sequence and is an RNA sequence consisting of U (uracil) instead of T (thymine) among the corresponding protospacer sequences. In this case, the guide sequence has complete complementarity with respect to the protospacer sequence or has at least 60, 70, 80, 90%, or more complementarity. As an example, the guide sequence may be 5 to 30 base sequences. As an example, the guide sequence may be 10 to 25 base sequences.

The first complementary sequence may be derived from a first complementary sequence derived from a natural origin, or may include a sequence having sequence identity therewith. AS an example, the first complementary sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the first complementary sequence may include 5'-GUUUUAGAGCUA-3' (SEQ ID NO: 270), or may include a sequence having at least 50% sequence identity therewith. As another specific example, when derived from *Campylobacter jejuni*, the first complementary sequence may include 5'-GUUUUAGUCCC-UUUUUAAAUUUCUU-3' (SEQ ID NO: 271) or 5'-GUUUUAGUCCCUU-3' (SEQ ID NO: 272), or may include a sequence having at least 50% sequence identity therewith.

tracrRNA

The tracrRNA includes a second complementary sequence for complementary binding to the crRNA.

The second complementary sequence may be derived from a naturally occurring second complementary sequence, or may include a sequence having sequence identity therewith. As an example, the second complementary sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the second complementary sequence may include 5'-UAGCAAGUUAAAAU-3' (SEQ ID NO: 273), or may include a sequence having at least 50% sequence identity therewith. As another specific example, when derived from *Campylobacter jejuni*, the second complementary sequence may include 5'-AAGAAAUUUAAAAAGGGACUAAAAU-3' (SEQ ID NO: 274) or 5'-AAGGGACUAAAAU-3' (SEQ ID NO: 275), or may include a sequence having at least 50% sequence identity therewith.

The tracrRNA may further comprise a tail sequence.

The tail sequence may be derived from a naturally occurring tail sequence, or may include a sequence having sequence identity therewith. AS an example, the tail sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the tail sequence may include 5'-UUAUCAACUUGAAAAAGUGGCACCGAGUCGGUGC-3' (SEQ ID NO: 276), or may include a sequence having at least 50% sequence identity therewith. As another specific example, when derived from *Campylobacter jejuni*, the tail sequence may include 5'-GGGACUCUGCGGGGGUUACAAUCCCCUAAAACCGCUUUU-3' (SEQ ID NO: 277), or may include a sequence having at least 50% sequence identity therewith.

Cas Protein

Cas protein, as used herein, refers to a protein capable of cleaving DNA in a cell.

As an example, the Cas protein may be at least one selected from the group consisting of *Streptococcus pyogenes*-derived Cas9 protein, *Campylobacter jejuni*-derived Cas9 protein, *Streptococcus thermophiles*-derived Cas9 protein, *Staphylococcus aureus*-derived Cas9 protein, *Neisseria meningitidis*-derived Cas9 protein, and Cpf1. The Cas protein includes an artificially modified protein in addition to the wild-type protein.

The Cas protein may comprise a domain capable of cleaving DNA and a domain recognizing a PAM sequence.

The domain capable of cleaving DNA can cleave both strands of DNA. Alternatively, only the strand that interacts with the guide sequence may be cleaved. Alternatively, only the complementary strand of the strand interacting with the guide sequence may be cleaved. Also, the DNA cleavage method may be different depending on the type of Cas protein. As an example, the Cas9 protein can cut two DNA strands side by side. As another example, the Cpf1 protein may not cut two DNA strands side by side.

A domain recognizing a PAM sequence may have a different recognized PAM sequence depending on the type of Cas protein. As an example, the Cas9 protein derived from *Streptococcus pyogenes* may recognize the PAM sequence of 5'-NGG-3' (N is A, T, C, or G).

The Cas protein may interact with a guide RNA. The Cas protein may interact with the guide RNA to form a guide RNA-Cas protein complex. As an example, the Cas9 protein may interact with a guide RNA including both crRNA and tracrRNA. As another example, the Cpf1 protein may interact with a guide RNA that does not include tracrRNA.

PAM Sequence

As used herein, a PAM sequence is a base sequence present in DNA, and the PAM sequence may be recognized by a Cas protein. Recognizing the PAM sequence of the Cas protein may affect the DNA cleavage function of the Cas protein.

The PAM sequence exists in a strand in which a protospacer sequence exists in the target region.

The PAM sequence may have a different sequence depending on the origin of the Cas protein.

As an example, the PAM sequence may be one of 5'-NGG-3' (N is A, T, C, or G), 5'-NNGRR(N)-3' (N is each independently A, T, C, or G, and R is A or G), 5'-TTN-3' (N is A, T, C, or G), 5'-NNNNGATT-3' (N is A, T, C, or G), 5'-NNAGAA-3' (N is A, T, C, or G), and the like.

Transgene

As used herein, a transgene may be a gene encoding a protein of interest. In the present disclosure, the transgene may be inserted into a genome of a cell to replace an existing protein or express a novel protein.

Unless defined otherwise, all technical and scientific terms used herein have the same meaning as commonly understood by those of ordinary skilled in the art to which this invention belongs. All publications, patents, and other references mentioned herein are incorporated by reference in their entirety.

Hereinafter, specific details of the present invention will be disclosed.

I. Genetically Modified Cell Selection Method

An example disclosed in the present disclosure is a method for sorting out a cell including a modified gene at a target locus in the genome. The method uses a fluorescent cell to sorting out a genetically modified cell without an additional analysis process. The fluorescent cell refers to a cell expressing a fluorescent protein gene by including the fluorescent protein gene in the genome of the cell.

In one embodiment, the method comprises the following steps.

(a) preparing a fluorescent cell;
(b) treating the fluorescent cell with a composition; and
(c) selecting a non-fluorescent cell.

Each step will be described in detail below.

1. Preparing a Fluorescent Cell

In the present disclosure, in order to efficiently sort out the genetically modified cells without an additional analysis method, a cell expressing fluorescence (fluorescent cell) is used.

1) Fluorescent Cell that Expresses Fluorescence

The fluorescent cell disclosed in the present disclosure refers to a cell expressing a fluorescent protein gene by including the fluorescent protein gene in the genome of the cell.

i) Cells

As an example, the cell may be a non-human mammalian cell. As an example, the cell may be a cell of a cow, a pig, a mouse, a rat, and the like. As a specific example, the cell is a bovine cell.

As another example, the cell may be a somatic cell or a germ cell. As a specific example, the cell may be a fertilized egg obtained by the fertilization of a germ cell. As another specific example, the cell may be a blastocyst in which a fertilized egg is cell-divided.

ii) Fluorescent Protein Gene

The fluorescent protein gene is contained in the genome of the cell. As an example, the fluorescent protein gene is contained in a safe harbor in the genome of the cell. The safe harbor may include AAVS1, CCR5, ROSA26, ACTB, and the like. As another example, the fluorescent protein gene is included in an intron in the genome of a cell. As a specific example, when the cell is a bovine cell, the fluorescent protein gene may be included in one or more positions of 105665894 position of chromosome 1; 79750136 position of chromosome 3; 71122343 position of chromosome 4; 85854536 position of chromosome 10; 51221667 position of chromosome 12; 80581377 position of chromosome X; 95433564-95434563 positions of chromosome 4; 113823097-113823101 position of chromosome 4; and 20085913-20086912 position of chromosome 6 in the genome of the bovine cell. As an example, the fluorescent protein gene may be included in one or more positions of 95433564 position of chromosome 4; 113823097 position of chromosome 4; and 20085913 position of chromosome 6.

The fluorescent protein gene is present on one or more positions in the cell genome. As an example, the fluorescent protein gene is present on two positions in the cell genome. As an example, the fluorescent protein gene is present on three or more positions in the cell genome.

As an example, the fluorescent protein gene may be one or more among a green fluorescent protein gene (GFP), a blue fluorescent protein gene (BFP), a cyan fluorescent protein gene (CFP), a yellow fluorescent protein gene (YFP), a red fluorescent protein gene (RFP), and the like. As a specific example, the fluorescent protein gene is a green fluorescent protein gene.

iii) Relationship Between Fluorescent Protein Gene and Target Locus Gene

The fluorescent protein gene and an interest gene on the target locus in the cell genome are different genes. The fluorescent protein gene and the gene on the target locus in the cell genome exist on different positions.

In this case, the fluorescent cell may be prepared as a method of using a wild-type cell or an animal expressing a fluorescent protein gene.

2) Method of Using Wild-Type Cell i) Wild-Type Cell

In one aspect of the method of preparing the cell expressing fluorescence, a method of inserting a fluorescent protein gene into a wild-type cell may be used.

The wild-type cell may be a somatic cell or a germ cell. As an example, a fluorescent cell may be prepared by inserting a fluorescent protein gene into a somatic cell. As another example, a fluorescent cell may be prepared by inserting a fluorescent protein gene into a fertilized egg using germ cells. As another example, a fluorescent cell may be prepared by inserting a fluorescent protein gene into a blastocyst in which a fertilized egg is cell-divided.

ii) Method of Inserting a Fluorescent Protein Gene into a Wild-Type Cell

As a method of inserting the fluorescent protein gene, a method of using plasmid DNA or a virus, a method of using a transposon or a method of using gene scissors may be used. The method of using the transposon may be at least one of a using piggyBac transposon system and a sleeping beauty transposon system. The method of using the gene scissors may be a method of using one or more of specific target nucleases. As an example, the method of using the gene scissors may be one or more of methods of using zinc finger nuclease (ZFN), TALEN, and CRISPR-Cas.

In the method of inserting the fluorescent protein gene, the fluorescent protein gene may be inserted on one or more positions in the genome of a cell. As an example, the fluorescent protein gene may be inserted on two positions in the genome of a cell. As another example, the fluorescent protein gene may be inserted on three or more positions in the genome of a cell.

At this time, the fluorescent protein gene is inserted into the safe harbor in the genome of the cell. The safe harbor may include AAVS1, CCR5, ROSA26, ACTB, and the like. As an example, the fluorescent protein gene is inserted into an intron position in the genome of a cell. As a specific example, the fluorescent protein gene may be inserted on one or more positions in the genome of a bovine cell. As a specific example, the fluorescent protein gene may be inserted on at least one position of 105665894 position of chromosome 1; 79750136 position of chromosome 3; 71122343 position of chromosome 4; 85854536 position of chromosome 10; 51221667 position of chromosome 12; 80581377 position of chromosome X; 95433564-95434563 position of chromosome 4; 113823097-113823101 position of chromosome 4; and 20085913-20086912 position of chromosome 6 in the genome of a bovine cell. As an example, the fluorescent protein gene may be inserted into at least one position of 95433564 position of chromosome 4; 113823097 position of chromosome 4; and 20085913 position of chromosome 6.

3) Method of Using an Animal Expressing a Fluorescent Protein Gene i) An Animal Expressing a Fluorescent Protein Gene As another aspect of the method for preparing the cell expressing a fluorescence, a method using a transgenic animal expressing a fluorescent protein gene may be used. As an example, the animal expressing the fluorescent protein gene may be one or more of a cow, a pig, a mouse, a rat, and the like. As an example, a cow expressing the fluorescent protein gene may be used.

The animal expressing the fluorescent protein gene may be an animal expressing one or more genes among green fluorescent protein gene (GFP), blue fluorescent protein gene (BFP), cyan fluorescent protein gene (CFP), yellow fluorescent protein gene (YFP), red fluorescent protein gene (RFP), and the like. As an example, the animal expressing the green fluorescent protein gene may be used.

In the animal expressing the fluorescent protein gene, the fluorescent protein gene is inserted on one or more positions in the genome. As an example, an animal in which a fluorescent protein gene is inserted into a safe harbor in the genome may be used. The safe harbor may include AAVS1, CCR5, ROSA26, ACTB, and the like. As an example, an animal in which a fluorescent protein gene is inserted into an intron in the genome may be used. As a specific example, a cow in which the fluorescent protein gene is inserted into one or more positions among 105665894 position of chromosome 1; 79750136 position of chromosome 3; 71122343 position of chromosome 4; 85854536 position of chromosome 10; 51221667 position of chromosome 12; 80581377 position of chromosome X; 95433564-95434563 position of chromosome 4; 113823097-113823101 position of chromosome 4; and 20085913-20086912 position of chromosome 6 in the genome may be used. As an example, a cow in which the fluorescent protein gene is inserted into one or more positions among 95433564 position of chromosome 4; 113823097 position of chromosome 4; and 20085913 position of chromosome 6 may be used. As a specific example, a cow including a fluorescent protein gene described in the Yum S Y et al. literature (Long-term health and germline transmission in transgenic cattle following transposon-mediated gene transfer. BMC Genomics 2018; 19:387) may be used.

ii) Fluorescent Cell Prepared Using Animal Expressing Fluorescent Protein Gene

The fluorescent cell may be a somatic cell or a germ cell. As an example, a fluorescent cell may be prepared by separating a somatic cell from an animal expressing a fluorescent protein gene. As another example, a fluorescent cell may be prepared by separating a germ cell from an animal expressing a fluorescent protein gene. As a specific example, the fluorescent cell may be prepared by separating germ cells from an animal expressing a fluorescent protein gene and then using them to make fertilized eggs or blastocysts. As another specific example, the fluorescent cell may be prepared by separating germ cells from a cow including fluorescent protein gene described in the Yum S Y et al. literature (Long-term health and germline transmission in transgenic cattle following transposon-mediated gene transfer. BMC Genomics 2018; 19:387) and then using them to make fertilized eggs or blastocysts.

2. Treating the Fluorescent Cell with a Composition

In the present disclosure, the cell are treated with a composition.

1) Construction of Composition

The composition comprises i) a guide RNA for a gene on a target locus in the genome or a nucleic acid sequence encoding the same;

ii) a guide RNA for a fluorescent protein gene or a nucleic acid sequence encoding the same; and iii) Cas protein or a nucleic acid sequence encoding the same.

In this case, the composition may further comprise a transgene to be inserted into the target locus in the genome.

i) A Guide RNA (First Guide RNA) for the Gene on the Target Locus in the Genome

The composition includes a guide RNA for a gene on a target locus in a genome. The first guide RNA is a component for modifying the gene on the target locus in the genome.

The first guide RNA is a single guide RNA or a dual guide RNA. The first guide RNA may recognize the gene on the target locus in the genome of the cell and interact with a Cas protein.

The first guide RNA includes crRNA and/or tracrRNA.

The crRNA may include a first guide sequence and additionally include a first complementary sequence that binds complementary to tracrRNA.

The first guide sequence is a sequence having the same identity with a protospacer sequence, which is a sequence complementary to a target sequence of DNA in the cell, and is an RNA sequence composed of U (uracil) instead of T (thymine) among the corresponding protospacer sequences. In this case, the guide sequence has complete complementarity to the protospacer sequence or has at least 60, 70, 80, 90%, or more complementarity. As an example, the guide sequence may be 5 to 30 base sequences. As an example, the guide sequence may be 10 to 25 base sequences.

As an example, the first guide RNA may have a first guide sequence having the same identity with a protospacer sequence, which is a sequence complementary to a target sequence of a gene DNA to suppress expression. As another example, the first guide RNA may have a first guide sequence capable of interacting with a protospacer sequence, which is a sequence complementary to a target sequence of gene DNA present at a position into which a transgene is to be inserted.

As an example, the first guide RNA may have one or more guide sequences from SEQ ID NO: 1 to 150.

TABLE 1

Guide sequence of guide RNA for beta-lactoglobulin (BLG) gene

| Gudie Sequence (5' to 3') | SEQ ID NO |
|---|---|
| GGAGAUGUCGCUGGCCGCCA | 1 |
| GUACUCCUUGGCCAUGGCGGCCA | 2 |
| GCCAUGGCGGCCAGCGACAUCUC | 3 |
| AGCUCCUCCACAUACACUCUCAG | 4 |
| UGCAGCAGGAUCUCCAGGUCGCC | 5 |
| CUGCAGCAGGAUCUCCAGGUCGC | 6 |

TABLE 2

Guide sequence of guide RNA for prion (PRNP) gene

| Gudie Sequence (5' to 3') | SEQ ID NO |
|---|---|
| AUCAUGGUGAAAAGCCACAU | 7 |
| UGAAAAGCCACAUAGGCAGU | 8 |
| CCACAUAGGCAGUUGGAUCC | 9 |
| CCAGGAUCCAACUGCCUAUG | 10 |
| UUGGAUCCUGGUUCUCUUUG | 11 |
| ACAUGGCCACAAAGAGAACC | 12 |
| UGGUUCUCUUUGUGGCCAUG | 13 |
| UGUGGCCAUGUGGAGUGACG | 14 |
| GUGGCCAUGUGGAGUGACGU | 15 |
| GAGGCCCACGUCACUCCACA | 16 |
| GUUUUGGUCGCUUCUUGCAG | 17 |
| UGCAAGAAGCGACCAAAACC | 18 |
| AAGAAGCGACCAAAACCUGG | 19 |
| AAGCGACCAAAACCUGGAGG | 20 |
| GACCAAAACCUGGAGGAGGA | 21 |
| UUCCAUCCUCCUCCAGGUUU | 22 |
| CCUGGAGGAGGAUGGAACAC | 23 |
| CCAGUGUUCCAUCCUCCUCC | 24 |
| CUGGAGGAGGAUGGAACACU | 25 |
| UGGAGGAGGAUGGAACACUG | 26 |
| GGAGGAGGAUGGAACACUGG | 27 |
| GAGGAGGAUGGAACACUGGG | 28 |
| ACUGGGGGGAGCCGAUACCC | 29 |
| GGGGAGCCGAUACCCAGGAC | 30 |
| GGGAGCCGAUACCCAGGACA | 31 |
| GACUGCCCUGUCCUGGGUAU | 32 |

TABLE 2-continued

Guide sequence of guide RNA for prion (PRNP) gene

| Gudie Sequence (5' to 3') | SEQ ID NO |
|---|---|
| UACCCAGGACAGGGCAGUCC | 33 |
| CUCCAGGACUGCCCUGUCCU | 34 |
| CCAGGACAGGGCAGUCCUGG | 35 |
| CCUCCAGGACUGCCCUGUCC | 36 |
| GGUGGAUAACGGUUGCCUCC | 37 |
| AGGCAACCGUUAUCCACCUC | 38 |
| GGCAACCGUUAUCCACCUCA | 39 |
| AACCGUUAUCCACCUCAGGG | 40 |
| ACCGUUAUCCACCUCAGGGA | 41 |
| CCGUUAUCCACCUCAGGGAG | 42 |
| CCCCUCCCUGAGGUGGAUAA | 43 |
| CGUUAUCCACCUCAGGGAGG | 44 |
| UAUCCACCUCAGGGAGGGGG | 45 |
| CAGCCACCCCUCCCUGAGG | 46 |
| CACCUCAGGGAGGGGUGGC | 47 |
| ACCUCAGGGAGGGGUGGCU | 48 |
| CCUCAGGGAGGGGUGGCUG | 49 |
| CCCCAGCCACCCCUCCCUG | 50 |
| GGUGGCUGGGGUCAGCCCCA | 51 |
| GGCUGGGGUCAGCCCCAUGG | 52 |
| UGGGGUCAGCCCCAUGGAGG | 53 |
| GUCAGCCCCAUGGAGGUGGC | 54 |
| UCAGCCCCAUGGAGGUGGCU | 55 |
| CAGCCCCAUGGAGGUGGCUG | 56 |
| UGGCCCCAGCCACCUCCAUG | 57 |
| CUGGCCCCAGCCACCUCCAU | 58 |
| GCUGGCCCCAGCCACCUCCA | 59 |
| GGUGGCUGGGGCCAGCCUCA | 60 |
| GGCUGGGGCCAGCCUCAUGG | 61 |
| UGGGGCCAGCCUCAUGGAGG | 62 |
| GCCAGCCUCAUGGAGGUGGC | 63 |
| CCAGCCUCAUGGAGGUGGCU | 64 |
| CCCAGCCACCUCCAUGAGGC | 65 |
| CAGCCUCAUGGAGGUGGCUG | 66 |
| UGGCCCCAGCCACCUCCAUG | 67 |
| GGUGGCUGGGGCCAGCCUCA | 68 |
| GGCUGGGGCCAGCCUCAUGG | 69 |

TABLE 2-continued

Guide sequence of guide RNA for prion (PRNP) gene

| Gudie Sequence (5' to 3') | SEQ ID NO |
|---|---|
| UGGGGCCAGCCUCAUGGAGG | 70 |
| GCCAGCCUCAUGGAGGUGGC | 71 |
| CCAGCCUCAUGGAGGUGGCU | 72 |
| CCCAGCCACCUCCAUGAGGC | 73 |
| CAGCCUCAUGGAGGUGGCUG | 74 |
| UGACCCCAGCCACCUCCAUG | 75 |
| GGUGGCUGGGGUCAGCCCCA | 76 |
| GGCUGGGGUCAGCCCCAUGG | 77 |
| UGGGGUCAGCCCCAUGGUGG | 78 |
| GUCAGCCCCAUGGUGGUGGC | 79 |
| UCAGCCCCAUGGUGGUGGCU | 80 |
| CAGCCCCAUGGUGGUGGCUG | 81 |
| UGUCCCAGCCACCACCAUG | 82 |
| CUGUCCCCAGCCACCACCAU | 83 |
| GCUGUCCCCAGCCACCACCA | 84 |
| GGUGGCUGGGGACAGCCACA | 85 |
| GGCUGGGGACAGCCACAUGG | 86 |
| UGGGGACAGCCACAUGGUGG | 87 |
| GGACAGCCACAUGGUGGUGG | 88 |
| AGCCACAUGGUGGUGGAGGC | 89 |
| GCCACAUGGUGGUGGAGGCU | 90 |
| CCACAUGGUGGUGGAGGCUG | 91 |
| CCCCAGCCUCCACCACCAUG | 92 |
| GGUGGUGGAGGCUGGGGUCA | 93 |
| GGUGGAGGCUGGGGUCAAGG | 94 |
| UGGGGUCAAGGUGGUACCCA | 95 |
| AAGGUGGUACCCACGGUCAA | 96 |
| GGGUUUGUUCCAUUGACCGU | 97 |
| UGGGUUUGUUCCAUUGACCG | 98 |
| AUGUUGGUUUUUGGCUUACU | 99 |
| CAUGUUGGUUUUUGGCUUAC | 100 |
| ACAUGCUUCAUGUUGGUUUU | 101 |
| AAAAACCAACAUGAAGCAUG | 102 |
| ACCAACAUGAAGCAUGUGGC | 103 |
| UCCUGCCACAUGCUUCAUGU | 104 |
| GUGGCAGGAGCUGCUGCAGC | 105 |
| AGCUGCUGCAGCUGGAGCAG | 106 |

TABLE 2-continued

Guide sequence of guide RNA for prion (PRNP) gene

| Gudie Sequence (5' to 3') | SEQ ID NO |
|---|---|
| GCUGCAGCUGGAGCAGUGGU | 107 |
| CUGCAGCUGGAGCAGUGGUA | 108 |
| UGCAGCUGGAGCAGUGGUAG | 109 |
| GCAGCUGGAGCAGUGGUAGG | 110 |
| GGAGCAGUGGUAGGGGCCU | 111 |
| GCAGUGGUAGGGGCCUUGG | 112 |
| GGGCCUUGGUGGCUACAUGC | 113 |
| GGCCUUGGUGGCUACAUGCU | 114 |
| UUCCCAGCAUGUAGCCACCA | 115 |
| UGCUGGGAAGUGCCAUGAGC | 116 |
| AUGUAUAAGAGGCCUGCUCA | 117 |
| AGCAGGCCUCUUAUACAUUU | 118 |
| UCACUGCCAAAAUGUAUAAG | 119 |
| ACAUUUGGCAGUGACUAUG | 120 |
| GCAUGUUUUCACGAUAGUAA | 121 |
| AGUACACUUGGUUGGGGUAA | 122 |
| ACCCCAACCAAGUGUACUAC | 123 |
| GCCUGUAGUACACUUGGUUG | 124 |
| GGCCUGUAGUACACUUGGUU | 125 |
| UGGCCUGUAGUACACUUGGU | 126 |
| CCAAGUGUACUACAGGCCAG | 127 |
| CCACUGGCCUGUAGUACACU | 128 |
| UGGUUACUAUACUGAUCCAC | 129 |
| AGUCAUGCACAAAGUUGUUC | 130 |
| CUGUGUCAACAUCACAGUCA | 131 |
| CACAGUCACCACCACCACCA | 132 |
| ACAGUCACCACCACCACCAA | 133 |
| CAGUCACCACCACCACCAAG | 134 |
| AGUCACCACCACCACCAAGG | 135 |
| GUUCUCCCCUUGGUGGUGG | 136 |
| GAAGUUCUCCCCUUGGUGG | 137 |
| GGUGAAGUUCUCCCCCUUGG | 138 |
| UUCGGUGAAGUUCUCCCCCU | 139 |
| CAUCAUCUUGAUGUCAGUUU | 140 |
| CGAAACUGACAUCAAGAUGA | 141 |
| CAUCAAGAUGAUGGAGCGAG | 142 |
| CAAGAUGAUGGAGCGAGUGG | 143 |
| CUGGGAUUCUCUCUGGUACU | 144 |
| CCAGUACCAGAGAGAAUCCC | 145 |
| CCUGGGAUUCUCUCUGGUAC | 146 |
| AAUAAGCCUGGGAUUCUCUC | 147 |
| UCCCAGGCUUAUUACCAACG | 148 |
| CCCAGGCUUAUUACCAACGA | 149 |
| CCCUCGUUGGUAAUAAGCCU | 150 |

As a specific example, the first guide RNA has a first guide sequence of 5'-GGAGAUGUCGCUGGCCGCCA-3' (SEQ ID NO: 1). In another specific example, the first guide RNA has a first guide sequence of 5'-AAAAACCAA-CAUGAAGCAUG-3' (SEQ ID NO: 102).

The first complementary sequence included in the first guide RNA of the present disclosure may be derived from a naturally occurring first complementary sequence or may include a sequence having sequence identity therewith. As an example, the first complementary sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the first complementary sequence may include 5'-GUUUUAGAGCUA-3' (SEQ ID NO: 270) or may include a sequence having at least 50% sequence identity therewith. As another specific example, when derived from *Campylobacter jejuni*, the first complementary sequence may include 5'-GUUUUAGUCCC-UUUUUAAAUUUCUU-3' (SEQ ID NO: 271) or 5'-GUUUUAGUCCCUU-3' (SEQ ID NO: 272), or may include a sequence having at least 50% sequence identity therewith.

The tracrRNA included in the first guide RNA of the present disclosure comprises a second complementary sequence that complementarily binds to the crRNA.

The second complementary sequence may be derived from a naturally occurring second complementary sequence or may include a sequence having sequence identity therewith. AS an example, the second complementary sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the second complementary sequence may include 5'-UAGCAAGUUAAAAU-3' (SEQ ID NO: 273) or may include a sequence having at least 50% sequence identity therewith. As another specific example, when derived from *Campylobacter jejuni*, the second complementary sequence may include 5'-AAGAAAUUUAAAAAGGGACUAAAAU-3' (SEQ ID NO: 274) or 5'-AAGGGACUAAAAU-3' (SEQ ID NO: 275), or may include a sequence having at least 50% sequence identity therewith.

The tracrRNA included in the first guide RNA of the present disclosure may further comprise a tail sequence.

The tail sequence may be derived from a naturally occurring tail sequence or may include a sequence having sequence identity therewith. AS an example, the tail sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the tail sequence may include 5'-UUAUCAACUUGAAAAAGUGGCACCGA-GUCGGUGC-3' (SEQ ID NO: 276) or may include a sequence having at least 50% sequence identity therewith. As another specific example, when derived from *Campylobacter jejuni*, the tail sequence may include 5'-GGGACU-CUGCGGGGGUUACAAUCCCUAAAACCGCUUUU-3' (SEQ ID NO: 277) or may include a sequence having at least 50% sequence identity therewith.

Meanwhile, in another embodiment of the present disclosure, a DNA encoding the first guide RNA may be provided.

In this case, the DNA sequence encoding the first guide RNA is a sequence comprising a sequence encoding the first guide sequence, the DNA sequence may include at least one of the same DNA sequences (sequences in which U is changed to T in each sequence) as the RNA sequence of SEQ ID NOs: 1 to 150.

ii) A Guide RNA for Fluorescent Protein Gene (Second Guide RNA)

The composition comprises a guide RNA (second guide RNA) for a fluorescent protein gene. The second guide RNA is a component for modifying the fluorescent protein gene.

The second guide RNA may be in the form of a single guide RNA or a dual guide RNA.

The second guide RNA may recognize a fluorescent protein gene in a cell genome and interact with a Cas protein.

The second guide RNA comprises crRNA and/or tracrRNA.

The crRNA included in the second guide RNA of the present disclosure may comprise a second guide sequence and may further comprise a first complementary sequence that complementarily binds to the tracrRNA.

The second guide sequence is a sequence having the same identity as a protospacer sequence which is a sequence complementary to a target sequence of DNA in a cell, and is an RNA sequence composed of U (uracil) instead of T (thymine) among the corresponding protospacer sequences. In this case, the guide sequence has complete complementarity to the protospacer nucleotide sequence or has at least 60, 70, 80, 90%, or more complementarity. As an example, the guide sequence may be 5 to 30 base sequences. As an example, the guide sequence may be 10 to 25 base sequences.

As an example, the second guide RNA has a second guide sequence, and the second guide sequence may interact with a partial nucleotide sequence of a fluorescent protein gene in a cell genome. The second guide sequence is a sequence having the same identity as a protospacer sequence which is a sequence complementary to a target sequence of the fluorescent protein gene DNA in the cell genome, and is an RNA sequence composed of U (uracil) instead of T (thymine) among the corresponding protospacer sequences. In this case, the guide sequence has complete complementarity or at least 60, 70, 80, 90%, or more complementarity. The second guide sequence may be 10 to 25 base sequences.

As an example, the fluorescent protein gene may be one or more genes among a green fluorescent protein gene (GFP), a blue fluorescent protein gene (BFP), a cyan fluorescent protein gene (CFP), a yellow fluorescent protein gene (YFP), a red fluorescent protein gene (RFP), etc.

As an example, the second guide RNA may have one or more guide sequences among SEQ ID NOs 151 to 269.

TABLE 3

Guide sequence of guide RNA for green fluorescent protein (GFP) gene.

| Gudie Sequence (5' to 3') | SEQ ID NO |
|---|---|
| AAGGGCGAGGAGCUGUUCAC | 151 |
| AGGGCGAGGAGCUGUUCACC | 152 |
| GGGCGAGGAGCUGUUCACCG | 153 |
| CGAGGAGCUGUUCACCGGGG | 154 |
| CACCGGGGUGGUGCCCAUCC | 155 |
| GACCAGGAUGGGCACCACCC | 156 |
| GGUGCCCAUCCUGGUCGAGC | 157 |
| CCCAUCCUGGUCGAGCUGGA | 158 |
| CCGUCCAGCUCGACCAGGAU | 159 |
| GCCGUCCAGCUCGACCAGGA | 160 |
| CGUCGCCGUCCAGCUCGACC | 161 |
| GAGCUGGACGGCGACGUGAA | 162 |
| GGCCACAAGUUCAGCGUGUC | 163 |
| CGCCGGACACGCUGAACUUG | 164 |
| CAAGUUCAGCGUGUCCGGCG | 165 |
| AAGUUCAGCGUGUCCGGCGA | 166 |
| CAGCGUGUCCGGCGAGGGCG | 167 |
| AGCGUGUCCGGCGAGGGCGA | 168 |
| GGCAUCGCCCUCGCCCUCGC | 169 |
| GGCGAGGGCGAUGCCACCUA | 170 |
| CAGGGUCAGCUUGCCGUAGG | 171 |
| CUUCAGGGUCAGCUUGCCGU | 172 |
| GGUGGUGCAGAUGAACUUCA | 173 |
| CGGUGGUGCAGAUGAACUUC | 174 |
| CUGAAGUUCAUCUGCACCAC | 175 |
| GGGCACGGGCAGCUUGCCGG | 176 |
| CCGGCAAGCUGCCCGUGCCC | 177 |
| CCAGGGCACGGGCAGCUUGC | 178 |
| ACGAGGGUGGGCCAGGGCAC | 179 |
| CACGAGGGUGGGCCAGGGCA | 180 |
| GUGGUCACGAGGGUGGGCCA | 181 |
| GGUGGUCACGAGGGUGGGCC | 182 |
| GUCAGGGUGGUCACGAGGGU | 183 |
| GGUCAGGGUGGUCACGAGGG | 184 |

TABLE 3-continued

Guide sequence of guide RNA for green fluorescent protein (GFP) gene.

| Gudie Sequence(5' to 3') | SEQ ID NO |
|---|---|
| GUAGGUCAGGGUGGUCACGA | 185 |
| CGUAGGUCAGGGUGGUCACG | 186 |
| CUCGUGACCACCCUGACCUA | 187 |
| CUGCACGCCGUAGGUCAGGG | 188 |
| GCACUGCACGCCGUAGGUCA | 189 |
| AGCACUGCACGCCGUAGGUC | 190 |
| GCUGAAGCACUGCACGCCGU | 191 |
| GCUUCAUGUGGUCGGGGUAG | 192 |
| CGUGCUGCUUCAUGUGGUCG | 193 |
| UCGUGCUGCUUCAUGUGGUC | 194 |
| GUCGUGCUGCUUCAUGUGGU | 195 |
| AGAAGUCGUGCUGCUUCAUG | 196 |
| UUCAAGUCCGCCAUGCCCGA | 197 |
| GACGUAGCCUUCGGGCAUGG | 198 |
| CUGGACGUAGCCUUCGGGCA | 199 |
| CAUGCCCGAAGGCUACGUCC | 200 |
| CGCUCCUGGACGUAGCCUUC | 201 |
| GCGCUCCUGGACGUAGCCUU | 202 |
| UGAAGAAGAUGGUGCGCUCC | 203 |
| GGAGCGCACCAUCUUCUUCA | 204 |
| ACCAUCUUCUUCAAGGACGA | 205 |
| GCCGUCGUCCUUGAAGAAGA | 206 |
| CAACUACAAGACCCGCGCCG | 207 |
| CUCGAACUUCACCUCGGCGC | 208 |
| CCGCGCCGAGGUGAAGUUCG | 209 |
| CCUCGAACUUCACCUCGGCG | 210 |
| CGCGCCGAGGUGAAGUUCGA | 211 |
| GUCGCCCUCGAACUUCACCU | 212 |
| GAAGUUCGAGGGCGACACCC | 213 |
| CAGCUCGAUGCGGUUCACCA | 214 |
| UCAGCUCGAUGCGGUUCACC | 215 |
| GGUGAACCGCAUCGAGCUGA | 216 |
| GUGAACCGCAUCGAGCUGAA | 217 |
| CGAUGCCCUUCAGCUCGAUG | 218 |
| GCUGAAGGGCAUCGACUUCA | 219 |
| GAAGGGCAUCGACUUCAAGG | 220 |
| GGCAUCGACUUCAAGGAGGA | 221 |
| CAAGGAGGACGGCAACAUCC | 222 |
| AAGGAGGACGGCAACAUCCU | 223 |
| AGGAGGACGGCAACAUCCUG | 224 |
| CAACAUCCUGGGGCACAAGC | 225 |
| UGUACUCCAGCUUGUGCCCC | 226 |
| CAGCCACAACGUCUAUAUCA | 227 |
| CGGCCAUGAUAUAGACGUUG | 228 |
| AUGGCCGACAAGCAGAAGAA | 229 |
| GAUGCCGUUCUUCUGCUUGU | 230 |
| CAAGCAGAAGAACGGCAUCA | 231 |
| CAAGAUCCGCCACAACAUCG | 232 |
| AUCCGCCACAACAUCGAGGA | 233 |
| UGCCGUCCUCGAUGUUGUGG | 234 |
| CGCUGCCGUCCUCGAUGUUG | 235 |
| GGUGUUCUGCUGGUAGUGGU | 236 |
| UGGGGGUGUUCUGCUGGUAG | 237 |
| UACCAGCAGAACACCCCCAU | 238 |
| CGCCGAUGGGGGUGUUCUGC | 239 |
| CAGAACACCCCCAUCGGCGA | 240 |
| CACGGGGCCGUCGCCGAUGG | 241 |
| GCACGGGGCCGUCGCCGAUG | 242 |
| AGCACGGGGCCGUCGCCGAU | 243 |
| CAGCACGGGGCCGUCGCCGA | 244 |
| GGUUGUCGGGCAGCAGCACG | 245 |
| UGGUUGUCGGGCAGCAGCAC | 246 |
| GUGGUUGUCGGGCAGCAGCA | 247 |
| GUGCUCAGGUAGUGGUUGUC | 248 |
| GGUGCUCAGGUAGUGGUUGU | 249 |
| CGGACUGGGUGCUCAGGUAG | 250 |
| UCAGGGCGGACUGGGUGCUC | 251 |
| GUCUUUGCUCAGGGCGGACU | 252 |
| GGUCUUUGCUCAGGGCGGAC | 253 |
| GUUGGGGUCUUUGCUCAGGG | 254 |
| CUCGUUGGGGUCUUUGCUCA | 255 |
| UCUCGUUGGGGUCUUUGCUC | 256 |
| UGUGAUCGCGCUUCUCGUUG | 257 |
| AUGUGAUCGCGCUUCUCGUU | 258 |
| CAUGUGAUCGCGCUUCUCGU | 259 |

TABLE 3-continued

Guide sequence of guide RNA for green fluorescent protein (GFP) gene.

| Gudie Sequence(5' to 3') | SEQ ID NO |
|---|---|
| CAACGAGAAGCGCGAUCACA | 260 |
| GCGCGAUCACAUGGUCCUGC | 261 |
| CGGCGGUCACGAACUCCAGC | 262 |
| CUGGAGUUCGUGACCGCCGC | 263 |
| UGGAGUUCGUGACCGCCGCC | 264 |
| ACCGCCGCCGGGAUCACUCA | 265 |
| GCCGUGAGUGAUCCCGGCGG | 266 |
| CAUGCCGUGAGUGAUCCCGG | 267 |
| CGCCGGGAUCACUCACGGCA | 268 |
| GUCCAUGCCGUGAGUGAUCC | 269 |

As a specific example, the second guide RNA has a second guide sequence of 5'-CGUCGCCGUCCAG-CUCGACC-3' (SEQ ID NO: 161).

The first complementary sequence included in the second guide RNA of the present disclosure may be derived from a naturally occurring first complementary sequence or may include a sequence having sequence identity therewith. As an example, the first complementary sequence may include a sequence derived from *Streptococcus pyogenes, Campylobacter jejuni, Streptococcus thermophiles, Staphylococcus aureus* or *Neisseria meningitides* or the like, and may include a sequence having at least 50% sequence identity therewith. As a specific example, when derived from *Streptococcus pyogenes*, the first complementary sequence may include 5'-GUUUUAGAGCUA-3' (SEQ ID NO: 270) or may include a sequence having at least 50% sequence identity therewith. As another specific example, when derived from *Campylobacter jejuni*, the first complementary sequence may include 5'-GUUUUAGUCCC-UUUUUAAAUUUCUU-3' (SEQ ID NO: 271) or 5'-GUUUUAGUCCCUU-3' (SEQ ID NO: 272), or may include a sequence having at least 50% sequence identity therewith.

The tracrRNA included in the second guide RNA of the present disclosure comprises a second complementary sequence that complementarily binds to the crRNA.

The second complementary sequence may be derived from a naturally occurring second complementary sequence or may include a sequence having sequence identity therewith. As an example, the second complementary sequence may include a sequence derived from *Streptococcus pyogenes, Campylobacter jejuni, Streptococcus thermophiles, Staphylococcus aureus*, or *Neisseria meningitides* or the like, and may include a sequence having at least 50% sequence identity therewith. As a specific example, when derived from *Streptococcus pyogenes*, the second complementary sequence may include 5'-UAGCAAGUUAAAAU-3' or may include a sequence having at least 50% sequence identity therewith. As another specific example, when derived from *Campylobacter jejuni*, the second complementary sequence may include 5'-AAGAAAUUUAAAAAGGGAC-UAAAAU-3' (SEQ ID NO: 274) or 5'-AAGGGAC-UAAAAU-3' (SEQ ID NO: 275), or may include a sequence having at least 50% sequence identity therewith.

The tracrRNA included in the second guide RNA of the present disclosure may further comprise a tail sequence.

The tail sequence may be derived from a naturally occurring tail sequence or may include a sequence having sequence identity therewith. AS an example, the tail sequence may include a sequence derived from *Streptococcus pyogenes, Campylobacter jejuni, Streptococcus thermophiles, Staphylococcus aureus* or *Neisseria meningitides*, or the like, and may include a sequence having at least 50% sequence identity therewith. As a specific example, when derived from *Streptococcus pyogenes*, the tail sequence may include 5'-UUAUCAACUUGAAAAAGUGGCACCGA-GUCGGUGC-3' (SEQ ID NO: 276) or may include a sequence having at least 50% sequence identity therewith. As another specific example, when derived from *Campylobacter jejuni*, the tail sequence may include 5'-GGGACU-CUGCGGGGGUUACAAUCCCCUAAAACCGCUUUU-3' (SEQ ID NO: 277) or may include a sequence having at least 50% sequence identity therewith.

Meanwhile, in another embodiment of the present application, a DNA encoding the second guide RNA may be provided.

In this case, the DNA sequence encoding the second guide RNA is a sequence comprising a sequence encoding the second guide sequence, and may include at least one of the same DNA sequence (a sequence in which U is replaced by T in each sequence) as the RNA sequence of SEQ ID NO: 151 to 269.

iii) Cas Protein

The composition comprises a Cas protein.

The Cas protein is a protein that functions to cut DNA by being induced to a specific position in the genome by a guide RNA.

As an example, the Cas protein may be at least one selected from the group consisting of *Streptococcus pyogenes*-derived Cas9 protein, *Campylobacter jejuni*-derived Cas9 protein, *Streptococcus* thermophiles-derived Cas9 protein, *Staphylococcus aureus*-derived Cas9 protein, *Neisseria meningitidis*-derived Cas9 protein, and Cpf1.

The Cas protein may combine with a first guide RNA. The Cas protein combines with a first guide RNA and is induced to the gene position of the target locus in the genome. The Cas protein cuts a gene on a target locus in the genome.

As an example, when a gene on a target locus in the genome is cut, the cut is repaired by non-homologous end joining. Non-homologous end joining occurs when several bases are inserted or deleted (indels) in the process of joining the cleaved ends. Therefore, the gene on the target locus in the genome may be knocked out by indels in the process of non-homologous end joining.

As another example, when a template DNA of a homologous base sequence exists, repair occurs based on the homologous template DNA. Accordingly, when the composition includes a transgene to be inserted into a target locus in the genome, the transgene may be knocked-in into the cleaved position by homologous recombination.

The Cas protein may combine with the second guide RNA. The Cas protein combines with the second guide RNA and is induced to the fluorescent protein gene position. The Cas protein cuts the fluorescent protein gene. When the fluorescent protein gene is cut, the fluorescent protein gene may be knocked out by indel in the process of non-homologous end joining.

iv) A Transgene to be Inserted into the Target Locus in the Genome

The composition may further comprise a transgene to be inserted into a target locus in the genome.

The composition is used for a genetically modified cell selection method, wherein the genetic modification includes knock-in of a foreign gene on the genome in addition to knock-out of a gene on the genome in the cell. When the genetic modification means knock-in, the composition may further include a transgene to be inserted into a target locus in the genome. As an example, when a gene on a target locus in the genome is cut by a Cas protein, a transgene may be inserted at the position. As an example, after the gene is cut, repair occurs based on the template DNA of the homologous base sequence by homologous recombination. The transgene can be inserted into a target locus in the genome through this homologous recombination process. As an example, the transgene may include homology arms having homology with the gene sequence of the target locus in the genome to be inserted into the target locus in the genome by homogeneous recombination at both ends of the transgene.

2) Method of Treatment of the Composition i) Form of Composition

The first guide RNA, the second guide RNA, the Cas protein, and/or the transgene may be treated into cells separately or in combination.

In one embodiment, the composition of the present disclosure may include a ribonucleoprotein (RNP) form.

As an example, the first guide RNA, the second guide RNA, and the Cas protein may be treated into a cell in the form of a guide RNA-Cas protein complex. As a specific example, the guide RNA and the Cas protein may be treated into cells in the form of ribonucleoprotein (RNP). In this case, only the first guide RNA may be treated into the cell in the form of a guide RNA-Cas protein complex. In this case, only the second guide RNA may be treated into the cell in the form of a guide RNA-Cas protein complex. In this case, both the first guide RNA and the second guide RNA may be treated into the cell in the form of a guide RNA-Cas protein complex.

In another embodiment, the composition of the present disclosure may include a vector form.

The first guide RNA, the second guide RNA, the Cas protein and/or the transgene may be treated into cells in the form of DNA encoding the same, RNA, or a mixture thereof.

The vector may be a plasmid or a viral vector. In this case, the virus may be a retrovirus, a lentivirus, an adenovirus, an adeno-associated virus, a herpes virus, or the like.

In this case, the nucleic acid sequences encoding the first guide RNA, the second guide RNA, the Cas protein and/or the transgene may be included in one vector or included in multiple vectors. As an example, the nucleic acid sequences encoding the first guide RNA, the second guide RNA, the Cas protein, and/or the transgene may be included in separate vectors, respectively. As an example, the nucleic acid sequences encoding the first guide RNA, the second guide RNA, the Cas protein, and/or the transgene may all be included in one vector.

In another embodiment, the composition of the present disclosure may include a mixed form of a vector and a non-vector.

The first guide RNA, the second guide RNA, the Cas protein, and/or the transgene may be treated into a cell in a mixed form of its RNA, protein, or DNA encoding them.

In this case, a mixed form thereof may be treated into cells in the form of a combination of vector and non-vector.

ii) Method of Treatment of the Composition

The composition may be treated to cells by a method using a vector or a method using a non-vector. When the composition is treated by a method using a vector, the vector may be a viral vector or a non-viral vector.

In the case of treating the composition in the form of the non-viral vector and the non-vector, the composition may be treated into cells by one or more of methods using a microinjection method, an electroporation method, and LNP (lipid nanoparticles). As a specific example, in order to treat the composition, the composition may be treated through electroporation of guide RNA and Cas protein in the form of ribonucleoprotein (RNP).

3) The Order of Processing the Composition

The composition may be treated to the cells simultaneously or in a series sequence. As an example, the first guide RNA, the second guide RNA, and the Cas protein of the composition may be simultaneously treated into cells.

As another example, the guide RNA and the Cas protein may be separately treated. In this case, the first guide RNA and the second guide RNA are simultaneously treated. As an example, after the first guide RNA and the second guide RNA are treated, the Cas protein may be treated. As another example, after the Cas protein is treated, the first guide RNA and the second guide RNA may be treated.

When the composition additionally includes a transgene, the transgene may be treated into the cell simultaneously with the guide RNA and the Cas protein or may be treated in a series sequence. In this case, the first guide RNA and the second guide RNA are simultaneously treated. As an example, the transgene may be simultaneously treated with guide RNA and Cas protein. As another example, after the transgene is treated, the guide RNA and the Cas protein may be treated. As another example, the transgene may be treated between the treatment steps of the guide RNA and the Cas protein. As another example, after the guide RNA is treated, the Cas protein and the transgene may be simultaneously treated. As another example, after the Cas protein is treated, the guide RNA and the transgene may be simultaneously treated. However, the treatment order is not limited thereto.

4) Effect after Composition Treatment_Genetic Modification i) Knock-Out of the Gene on the Target Locus When the composition does not include a transgene, the gene on the target locus in the genome of the fluorescent cell is cut by the first guide RNA and Cas protein, and the cleavage is repaired by non-homologous end joining. At this time, non-homologous end joining occurs when several bases are inserted or deleted (indels) in the process of connecting the cut ends. Accordingly, the gene on the target locus in the genome includes indels of some bases. The gene on the target locus in the genome may be knocked out by the indels of some bases.

In addition, the fluorescent protein gene in the genome of the fluorescent cell is cut by the second guide RNA and the Cas protein, and the cleavage is repaired by non-homologous end joining. At this time, non-homologous end joining occurs when several bases are inserted or deleted (indels) in the process of connecting the cut ends. Accordingly, the fluorescent protein gene in the genome includes indels of some bases. The fluorescent protein gene in the genome may be knocked out by the indels of some bases.

As a specific example, when the composition comprises a first guide RNA for the bovine beta-lactoglobulin (BLG) gene, a second guide RNA for a green fluorescent protein gene, and a Cas protein, fluorescent bovine cells are treated with the composition. Then, the beta-lactoglobulin (BLG) gene and the green fluorescent protein gene of the fluorescent bovine cell may include indels of some bases and may be knocked out by indels of some bases.

ii) Knock-In of the Transgene

When the composition includes a transgene, the gene on the target locus in the genome of the fluorescent cell is cut by the first guide RNA and the Cas protein, and when template DNA with a homologous nucleotide sequence exists, repair occurs at the basis of the homologous template DNA. Accordingly, when the composition includes a transgene to be inserted into a target locus in the genome, the transgene may be inserted into the cleaved position by homologous recombination.

In addition, the fluorescent protein gene in the genome of the fluorescent cell is cleaved by the second guide RNA and the Cas protein, and the cleavage is repaired by non-homologous end joining. At this time, non-homologous end joining occurs when several bases are inserted or deleted (indels) in the process of connecting the cut ends. Accordingly, the fluorescent protein gene in the genome includes indels of some bases. The fluorescent protein gene in the genome may be knocked out by the indels of some bases.

As a specific example, when the composition includes a first guide RNA for a gene on a bovine target locus, a second guide RNA for a green fluorescent protein gene, a Cas protein, and a transgene to be inserted into the target locus, a fluorescent bovine cell is treated with the composition, then a transgene is inserted into a target locus of a fluorescent bovine cell, and then a green fluorescent protein gene may be knocked out.

3. Selecting Non-Fluorescent Cells

In the non-fluorescent cells after the composition treatment, the gene on the target locus and the fluorescent protein gene has been modified by the first guide RNA, the second guide RNA, the Cas protein and/or the transgene. Therefore, by selecting the non-fluorescent cells, it is possible to select the genetically modified cells.

That is, in the present disclosure, non-fluorescent cells (cells that do not express fluorescence) are selected after the composition treatment step to select genetically modified cells.

1) Characteristics of Non-Fluorescent Cells (Cells that do not Express Fluorescence)

The non-fluorescent cell is a cell in which a gene on a target locus and a fluorescent protein gene has been modified.

The modified gene on the target locus in the genome may be one or more of the genes in the cell genome except for the fluorescent protein gene. The fluorescent protein gene is a gene different from the gene on the target locus in the genome. The fluorescent protein gene and the gene on the target locus in the genome are present at different positions.

The modified gene may be, for example, one or more of the genes whose expression is to be suppressed. As another example, the modified gene may be one or more of the genes present at a position into which a transgene is to be inserted.

The non-fluorescent cell includes a modified gene on a target locus in the genome.

As an example, the gene on the target locus in the genome of the non-fluorescent cell includes indels of some bases. That is, in the non-fluorescent cell, the gene on the target locus in the genome is knocked out by the indels of some bases. As a specific example, when the cell is a bovine cell, the beta-lactoglobulin (BLG) gene in the non-fluorescent cell includes indels of some bases. That is, in the non-fluorescent cell, the beta-lactoglobulin (BLG) gene is knocked out by the indels of some bases. In another example, in the non-fluorescent cell, the prion (PRNP) gene includes indels of some bases. That is, in the non-fluorescent cell, the prion (PRNP) gene is knocked out by the indels of some of the bases.

As another example, in the non-fluorescent cell, a transgene may be inserted at a target locus in the genome. As a specific example, when the cell is a bovine cell, the non-fluorescent cell has a transgene inserted (knocked-in) into the beta-lactoglobulin (BLG) gene. As another example, the non-fluorescent cell has a transgene inserted (knocked-in) into the prion (PRNP) gene position.

The non-fluorescent cell includes a modified fluorescent protein gene in the genome. The modified fluorescent protein gene means that the fluorescent protein gene is knocked out. In the non-fluorescent cell, all fluorescent protein genes present in the genome of the cell are knocked out.

2) Method for Selecting Non-Fluorescent Cells

Various methods of analyzing fluorescence to select for non-fluorescent cells may be used. As an example, as a method for selecting non-fluorescent cells, a method using FACS or a method using a microscope may be used. As a specific example, by analyzing the light emitted by the fluorescent material stimulated by a laser beam, the non-fluorescent cell and the fluorescent cell may be classified, and the non-fluorescent cell may be selected. As another specific example, non-fluorescent cells may be selected using fluorescence observation through a microscope.

4. Specific Example Beta-Lactoglobulin (BLG) Genetically Modified Cell Selection Method 1) Preparation of Fluorescent Cells Prepare cells including a green fluorescent protein (GFP) gene in the genome of a bovine cell.

2) Composition Treatment

The fluorescent bovine cells are treated with guide RNA having at least one guide sequence of SEQ ID Nos: 1 to 6 (guide RNA for BLG gene), guide RNA having at least one guide sequence of SEQ ID Nos: 151 to 269 (guide RNA for GFP gene) and Cas9 protein.

3) Non-Fluorescent Cell Selection

Cells that do not express fluorescence after treatment with the composition are selected. The cells that do not express the fluorescence (non-fluorescent cells) are cells in which the beta-lactoglobulin gene and the green fluorescent protein gene contain indels of some bases and are knocked out by the indels of some bases.

Through the above method, genetically modified cells may be efficiently selected.

II. Characteristics of the Genetically Modified Cell Selection Method

As an example, the present specification discloses a method for sorting out genetically modified cells. The method for sorting out genetically modified cells disclosed herein has the following characteristics.

First, the method uses a cell expressing fluorescence, a first guide RNA for a gene on a target locus, a second guide RNA for a fluorescent protein gene, and a Cas protein.

In this case, the method has the characteristic of treating material for modifying a gene on a target locus and a material for modifying a fluorescent protein gene in a cell expressing fluorescence through one single experimental process. Due to these characteristics, by using the method, two results of genetic modification of a target locus of a cell and genetic modification of a fluorescent protein may be obtained at the same time. That is, by using the method, cells in which the gene on the target locus is modified may be selected through the selection of non-fluorescent cells. Therefore, an additional analysis process for cell selection is not required. Conventionally, in order to check whether the cell is genetically modified, the gene on the target locus is PCR amplified and sequenced. However, the method for sorting out genetically modified cells disclosed herein does not require an additional sequencing step, so it is possible to avoid consuming time and effort for sequencing.

Second, in the method, cells are not consumed in the process of selecting genetically modified cells.

The conventional method of PCR amplification and sequencing of genes on the target locus is a method in which cells are consumed, and there is a problem in that cells that have undergone the sequencing step are not utilized and consumed thereafter. However, the method for sorting out genetically modified cells disclosed in the present disclosure is a method using fluorescence expression of cells and does not cause a problem in that cells are consumed in order to check and select whether cell is genetically modified or not.

III. Genetically Modified Cells

Disclosed herein are genetically modified cells.

As an example, the genetically modified cell disclosed herein is a cell selected through the method for sorting out genetically modified cells.

As an example, the genetically modified cell disclosed herein is a cell in which a gene on a target locus and a fluorescent protein gene in the genome has been modified.

The genetically modified cells may be interchanged with non-fluorescent cells.

1. Cell

The genetically modified cells disclosed herein may be one or more of the non-human mammalian cells. As a specific example, the cell may be one or more of bovine, pig, mouse, and rat cells. As a specific example, the cell is a bovine cell.

As another example, the cell may be a somatic cell or a germ cell. As a specific example, the cell is a fertilized egg or blastocyst generated through the fertilization of a germ cell. As another specific example, the cell may be a cell in which a nucleus of a somatic cell is transplanted into an enucleated egg.

2. Cells Including the Modified Gene on the Target Locus

The genetically modified cell disclosed herein is a cell in which a gene on a target locus in the genome has been modified.

In this case, the gene on the target locus may be one or more of the genes whose expression is to be suppressed. Alternatively, the gene on the target locus may be one or more of the genes present at a position into which a transgene is to be inserted.

As an example, in the cell, a gene on a target locus in the genome is knocked out. As a specific example, when the cell is a bovine cell, the non-fluorescent cell has a beta-lactoglobulin (BLG) gene knocked out. As another example, the non-fluorescent cell has a prion (PRNP) gene knocked out. The knock-out gene has a reduced function of the gene so that the expression of the gene in the cell is not detectably small or is not expressed.

As another example, in the non-fluorescent cell, a transgene is inserted at a target locus in the genome. As a specific example, the cell may be a cell in which a transgene is knocked-in at a target locus in the genome to replace an existing protein or to express a new protein. As an example, when the cell is a bovine cell, the non-fluorescent cell has a transgene inserted (knock-in) into the beta-lactoglobulin (BLG) gene position. As another example, the non-fluorescent cell has a transgene inserted (knock-in) into the prion (PRNP) gene position.

3. Cells in which the Fluorescent Protein Gene has been Modified

The genetically modified cell disclosed herein is a cell in which a fluorescent protein gene in the genome has been modified. In this case, the fluorescent protein gene is not located at the target locus in the genome.

The cell is a cell in which the fluorescent protein gene in the cell genome is knocked out. The cell is a cell in which the function of the fluorescent protein gene is reduced such that the expression of the fluorescent protein gene in the cell is not detectably small or is not expressed.

As an example, the modified fluorescent protein gene is present at one or more positions in the genome. As an example, the modified fluorescent protein gene is present at two positions in the genome. As an example, the modified fluorescent protein gene is present at three or more positions in the genome. As a specific example when the cell is a bovine cell, the modified fluorescent protein gene includes at least one of the 105665894 position of chromosome 1; 79750136 position of chromosome 3; 71122343 position of chromosome 4; 85854536 position of chromosome 10; 51221667 position of chromosome 12; 80581377 position of chromosome X; 95433564-95434563 position of chromosome 4; 113823097-113823101 position of chromosome 4; and 20085913-20086912 position of chromosome 6 in the genome. As an example, the modified fluorescent protein gene includes at least one of 95433564 position of chromosome 4; 113823097 position of chromosome 4; and 20085913 position of chromosome 6.

The cell is a cell in which all fluorescent protein genes present in the cell genome are knocked out. As an example, if the cell includes one fluorescent protein gene, one fluorescent protein gene is knocked out. As another example, if the cell includes two fluorescent protein genes, the two fluorescent protein genes are knocked out. As another example, if the cell includes three or more fluorescent protein genes, all three or more fluorescent protein genes are knocked out.

As an example, the fluorescent protein gene may be one or more among a green fluorescent protein gene (GFP), a blue fluorescent protein gene (BFP), a cyan fluorescent protein gene (CFP), a yellow fluorescent protein gene (YFP), a red fluorescent protein gene (RFP), etc. As a specific example, the fluorescent protein gene is a green fluorescent protein gene.

IV. Methods for Producing Genetically Modified Animals

Disclosed herein is a method for producing a genetically modified animal including a modified gene on a target locus in a genome.

The method for producing a genetically modified animal disclosed herein includes
  a) preparing a cells expressing fluorescence;
  b) treating the cell expressing the fluorescence with a composition;
  c) selecting a non-fluorescent cell; and
  d) implanting the non-fluorescent cell into the uterus of a surrogate mother.

Hereinafter, each step will be described in detail.

1. Preparing a Cells Expressing Fluorescence

In the present disclosure, in order to efficiently produce a genetically modified animal in which a gene is modified, a cell expressing fluorescence is used. The cell expressing the fluorescence is a cell expressing the fluorescent protein gene by including the fluorescent protein gene in the genome.

The description of preparing the cell expressing fluorescence disclosed in 1. Preparing a fluorescent cell of I. Genetically modified cell selection method) above are applied.

2. Treating the Cell Expressing the Fluorescence with the Composition

In the present disclosure, the cell is treated with a composition.

The description of the step of treating the composition disclosed in 2. Treating the fluorescent cell with a composition of I. Genetically modified cell selection method above is applied.

3. Selecting a Non-Fluorescent Cell (a Cell that does not Display Fluorescence) after Treatment with the Composition In the present disclosure, a non-fluorescent cell is selected after the cell is treated with the composition.

The description of the step of selecting the non-fluorescent cell disclosed in 3. Selecting non-fluorescent cells after treatment with the composition of I. Genetically modified cell selection method above is applied.

4. Transplanting the Non-Fluorescent Cell into the Uterus of a Surrogate Mother

In the present disclosure, after selecting the non-fluorescent cell to produce a genetically modified animal, the non-fluorescent cell is transplanted into the uterus of a surrogate mother.

In the step of transplanting the non-fluorescent cell into the uterus of the surrogate mother, the process of culturing the non-fluorescent cell in a transplantable state into the surrogate mother may be included.

1) Preparation of Transplantable Cells into Surrogate Mothers

When the non-fluorescent cell is a fertilized egg, the non-fluorescent cell can be cultured in a state capable of being transplanted into the surrogate mother and then transplanted into the uterus of the surrogate mother. As an example, after culturing the fertilized egg to a blastocyst stage, the fertilized egg may be transplanted into the uterus of a surrogate mother.

When the non-fluorescent cell is a somatic cell, a somatic cell nuclear transfer (SCNT) fertilized egg may be prepared and implanted in the uterus of a surrogate mother.

i) Method for Generating a Nuclear-Transferred Fertilized Egg

The nuclear-transferred fertilized egg includes the nucleus of the non-fluorescent somatic cell. The method for generating the nuclear-transferred fertilized egg may include nuclear removal of the egg, nuclear transfer of non-fluorescent somatic cells, and induction of cell fusion after transplantation. Hereinafter, a method for generating a nuclear-transferred fertilized egg using a known technique will be briefly described.

Egg type—The method may use an egg obtained from a wild-type animal or an egg obtained from an animal expressing a fluorescent protein gene.

Egg preparation—The method may use mature eggs that have undergone in vitro maturation after obtaining immature eggs from animals.

Nucleus Removal—The method may utilize a micropipette to remove the nucleus from a mature egg. As an example, a portion of the cytoplasm and nucleus of an egg may be removed using a micropipette.

Nuclear transfer—The method may include injecting donor cells of nuclear transfer into an egg. As an example, the method may use the non-fluorescent cells as donor cells of nuclear transfer.

Cell fusion—The method may include a process of applying a stimulus to a nuclear-transferred oocyte to achieve cell fusion between the cytoplasm of the enucleated oocyte and the nucleus of a donor cell. As an example, the stimulation may include electrical stimulation.

2) Transplantation

The cells described above are transplanted into a surrogate mother. As an example, the cells are transplanted into an animal of the same species as the cells. As a specific example, when the cells are bovine cells, the cells are transplanted into a cow.

The cells are transplanted into the uterus of a surrogate mother animal. As an example, the cells are transplanted into the uterine horn. As a specific example, cells are transplanted into the uterine horn without damaging the cervix and the uterus.

The step of transplanting the non-fluorescent cell into the uterus of the surrogate mother may further include determining pregnancy after transplantation. As an example, rectal examination or ultrasonography may be used to determine embryo survival and pregnancy. As a specific example, on the 45th day after estrus, it is possible to determine the pregnancy of a cow by rectal examination and/or ultrasonography.

5. Production of Animal

An animal born after being transplanted into a surrogate mother animal through the above process is an animal in which the gene on the target locus and the fluorescent protein gene in the genome have been modified. As an example, the gene on the target locus and the fluorescent protein gene in the genome of the animal born through the above process are knocked out. As another example, in animals born through the above process, a transgene is knocked in on a target locus in the genome, and a fluorescent protein gene is knocked out. As a specific example, in a cow born through using the above method, the bovine prion (PRNP) gene and fluorescent protein gene are mutated. As another specific example, in a cow born through using the above process, the bovine beta-lactoglobulin (BLG) gene and fluorescent protein gene are knocked out.

V. Genetically Modified Animals

Disclosed herein are genetically modified animals.

The genetically modified animal is an animal including a modified gene on a target locus in the genome.

1. Animal

The genetically modified animal disclosed herein may be one or more of the non-human mammals. As a specific example, the cell may be one or more cells of a cow, a pig, a mouse, and a rat. As a specific example, the animal is a cow.

2. Animal Including the Modified Gene on the Target Locus

The genetically modified animal disclosed herein has a cell in which a gene on a target locus in a genome has been modified.

In this case, the gene on the target locus may be one or more of the genes whose expression is to be suppressed. Alternatively, the gene on the target locus may be one or more of the genes present at a position into which a transgene is to be inserted.

As an example, the animal may be an animal in which a gene on a target locus in the genome is cut and knocked out. As a specific example, when the animal is a cow, a beta-lactoglobulin (BLG) gene or a prion (PRNP) protein gene is mutated in the animal. The knock-out gene has a reduced function of the gene so that the expression of the gene in the cell is not detectably small or is not expressed.

As another example, the animal may be an animal in which a gene on a target locus in the genome is cut, and a transgene is inserted into the cleaved site. As a specific example, the cell may be an animal in which a transgene is knocked in on a target locus in the genome to replace an existing protein or to express a new protein. As an example, when the animal is a cow, the animal may have a transgene inserted (knock-in) on the beta-lactoglobulin (BLG) gene position. As another example, the animal may have a transgene inserted (knock-in) on the prion (PRNP) gene position.

3. Cells in which the Fluorescent Protein Gene has been Modified

The genetically modified animal disclosed herein is a cell in which a fluorescent protein gene in the genome has been modified. In this case, the fluorescent protein gene is a gene different from the gene on the target locus in the genome.

The animal is an animal in which a fluorescent protein gene in the genome is knocked out. The animal is an animal in which the function of the fluorescent protein gene is reduced such that the expression of the fluorescent protein gene is not detectably small or is not expressed in the cell.

As an example, the modified fluorescent protein gene is present at one or more positions in the genome. As an example, the modified fluorescent protein gene is present at two positions in the genome. As an example, the modified fluorescent protein gene is present at three or more positions in the genome. As a specific example, when the animal is a cow, the modified fluorescent protein gene includes at least one of the 105665894 position of chromosome 1; 79750136 position of chromosome 3; 71122343 position of chromosome 4; 85854536 position of chromosome 10; 51221667 position of chromosome 12; 80581377 position of chromosome X; 95433564-95434563 position of chromosome 4; 113823097-113823101 position of chromosome 4; and 20085913-20086912 position of chromosome 6 in the genome. As an example, the modified fluorescent protein gene includes at least one of 95433564 position of chromosome 4; 113823097 position of chromosome 4; and 20085913 position of chromosome 6.

The animal is an animal in which all fluorescent protein genes present in the genome are knocked out. As an example, if one fluorescent protein gene is included in the genome of the animal, one fluorescent protein gene is knocked out. As another example, if two fluorescent protein genes are included in the genome of the animal, both fluorescent protein genes are knocked out. As another example, if three or more fluorescent protein genes are included in the genome of the animal, all three or more fluorescent protein genes are knocked out.

As an example, the fluorescent protein gene may be one or more among a green fluorescent protein gene (GFP), a blue fluorescent protein gene (BFP), a cyan fluorescent protein gene (CFP), a yellow fluorescent protein gene (YFP), a red fluorescent protein gene (RFP), etc. As a specific example, the fluorescent protein gene is a green fluorescent protein gene.

Fluorescent protein genes in the animal may be transferred to the same site in the next generation. As an example, when the animal is a cow, the fluorescent protein gene in the cow's genome may be transferred to the same site in the next generation.

VI. Kit for Selection of Genetically Modified Cells

Another example disclosed by the present disclosure is a kit for sorting out a cell including a modified gene on a target locus in the genome. Each component of the kit has the same meaning as the component used in the method for selecting genetically modified cells disclosed herein.

The kit disclosed in the present disclosure includes
i) a cell that express fluorescence;
ii) a guide RNA for a fluorescent protein gene or a nucleic acid encoding the same; and
iii) Cas protein or a nucleic acid encoding the same.

The kit may further include a guide RNA for a gene on a target locus in the genome or a nucleic acid encoding the same.

In addition, the kit may further include a transgene to be inserted into the target locus in the genome.

1. Cells that Express Fluorescence

A kit for sorting out a cell in which a gene on a target locus in a genome has been modified as disclosed in the present disclosure includes a cell expressing fluorescence.

1) Cells

As an example, the cell may be a non-human mammalian cell. As an example, the cell may be a cell of a cow, a pig, a mouse, or a rat. As a specific example, the cell is a bovine cell.

As another example, the cell may be a somatic cell or a germ cell. As a specific example, the cell is a blastocyst generated through the fertilization of germ cells. As another specific example, the cell is a cell in which a nucleus of a somatic cell is transplanted into an enucleated egg.

2) Fluorescent Protein

The cell is a cell that expresses fluorescence. The cell includes a fluorescent protein gene in the genome. As an example, the fluorescent protein gene may be one or more genes among a green fluorescent protein gene (GFP), a blue fluorescent protein gene (BFP), a cyan fluorescent protein gene (CFP), a yellow fluorescent protein gene (YFP), a red fluorescent protein gene (RFP), etc. As a specific example, the fluorescent protein gene is a green fluorescent protein gene.

The fluorescent protein gene is present in the cell genome. As an example, the fluorescent protein gene is present in a safe harbor in the genome of the cell. The safe harbor may include AAVS1, CCR5, ROSA26, ACTB, and the like. As an example, the fluorescent protein gene is present in an intron in the genome of a cell. As a specific example, when the cell is a bovine cell, the fluorescent protein gene is present on one or more positions among 105665894 position of chromosome 1; 79750136 position of chromosome 3; 71122343 position of chromosome 4; 85854536 position of chromosome 10; 51221667 position of chromosome 12; 80581377 position of chromosome X; 95433564-95434563 position of chromosome 4; 113823097-113823101 position of chromosome 4; and 20085913-20086912 position of chromosome 6 in the genome of the bovine cell. As an example, the fluorescent protein gene is present on one or more positions among 95433564position of chromosome 4; 113823097 position of chromosome 4; and 20085913 position of chromosome 6.

The fluorescent protein gene is present on one or more positions in the cell genome. As an example, the fluorescent protein gene is present on three positions in the cell genome.

The fluorescent protein gene is not present on a target locus in the cell genome. The fluorescent protein gene and the gene on the target locus in the cell genome exist in different positions.

3) Storage

The Cell expressing fluorescence, which is a component of the kit, may be stored in an appropriate environment for the storage of cells. As an example, the cell may be stored frozen in an appropriate medium according to the cell type, and the medium may contain a cryopreservative agent. As a specific example, the cell may be stored in a medium including a cryopreservative agent and stored at about −60° C. to −80° C. in a deep freezer. As another specific example, the cell may be stored in a medium including a cryopreservative agent and stored at about −180° C. to −200° C. in a liquid nitrogen tank.

2. Guide RNA for Fluorescent Protein Gene or Nucleic Acid Encoding the Same

The kit disclosed in the present disclosure includes a guide RNA (second guide RNA) for a fluorescent protein gene or a nucleic acid encoding the same.

1) Guide RNA

The second guide RNA is a single guide RNA or a dual guide RNA. The second guide RNA may recognize a fluorescent protein gene in a cell genome and may interact with a Cas protein. The second guide RNA includes a region capable of combining with a Cas protein. The guide RNA combines to the Cas protein and induces the Cas protein to the fluorescent protein gene position so that the fluorescent protein gene can be cut.

2) Storage

The second guide RNA, which is a component of the kit, may be stored in an appropriate environment for RNA storage. As an example, the second guide RNA may be stored in a dried state or in a buffer solution. As a specific example, the second guide RNA may be stored at −20° C. in a dried state or in a buffer solution.

3. Cas Protein or Nucleic Acid Encoding the Same

The kit disclosed in the present disclosure comprises a Cas protein or a nucleic acid encoding the same.

1) Cas Protein

The Cas protein may combine with a guide RNA. The Cas protein may be induced to the gene on the target locus in the genome by the guide RNA, thereby allowing the gene on the target locus in the genome to be cut. As an example, the Cas protein is a Cas9 protein or a Cpf1 protein. However, the present disclosure is not limited thereto.

2) Storage

The Cas protein, which is a component of the kit, may be stored in an appropriate environment to maintain nuclease activity. As an example, the Cas protein may be stored in a dried state or in a buffer solution. As a specific example, the Cas protein may be stored at −20° C. in a dried state or in a buffer solution.

4. Guide RNA for the Gene on the Target Locus in the Genome or Nucleic Acid Encoding the Same The kit disclosed in the present disclosure may further include a guide RNA (first guide RNA) for a gene on a target locus in the genome or a nucleic acid encoding the same.

1) First Guide RNA

The first guide RNA is a single guide RNA or a dual guide RNA. The first guide RNA may recognize a gene on a target locus in a cell genome and interact with a Cas protein. The first guide RNA includes a region capable of combining with a Cas protein. The guide RNA combines with the Cas protein and induces the Cas protein to the gene location of the target locus in the cell genome, thereby allowing the gene on the target locus to be cut.

2) Storage

The first guide RNA, which is a component of the kit, may be stored in an appropriate environment for RNA storage. As an example, the first guide RNA may be stored in a dried state or in a buffer solution. As a specific example, the first guide RNA may be stored at −20° C. in a dried state or in a buffer solution.

5. Transgene to be Inserted into the Target Locus in the Genome

The kit disclosed in the present disclosure may further include a transgene to be inserted into a target locus in the genome.

1) Transgene

In the genetically modified cell selection method disclosed in the present disclosure, genetic modification may include knock-in in addition to knock-out. When the genetic modification means knock-in, the kit for selecting cells in which the gene on the target locus in the genome is modified may further include a transgene to be inserted into the target locus in the genome. As an example, the transgene may be inserted into a target locus in the genome by homologous recombination.

2) Storage

The transgene, which is a component of the kit, may be stored in an appropriate environment for storing the transgene. As an example, the transgene may be stored in a dried state or in a buffer solution. As a specific example, the transgene may be stored at −20° C. in a dried state or in a buffer solution.

EXAMPLE

Example 1. Fluorescent Cow Production

For a fluorescent cow production method, the full text of Yum S Y et al. literature (Long-term health and germline transmission in transmission following transposon-mediated gene transfer. BMC Genomics 2018; 19:387) is referenced.

Example 1-1. DNA Vector

GFP was amplified by gateway PCR cloning (MultiSite Gateway Pro Plus, Invitrogen, 12537100, Life Technologies, Carlsbad, CA, USA) and inserted into a final expression vector, PB-CAG (www.addgene.org/, #20960).

Example 1-2. Egg Collection and In Vitro Maturation (IVM)

Ovaries were collected in saline at 35° C. in the slaughterhouse and transported to the laboratory within 2 hours. The cumulus-oocyte complex (COC) from follicles with a diameter of 2 to 8 mm was aspirated by using an 18 gauge needle attached to a 10 ml disposable syringe. COCs with evenly granulated cytoplasm and surrounded by three or more layers of compact cumulus cells were selected and washed three times in HEPES buffered tissue culture medium-199 (TCM-199; Invitrogen, Carlsbad, CA, USA) supplemented with 10% FBS, 2 mM $NaHCO_3$(Sigma-Aldrich Corp., St. Louis, MO, USA), and 1% penicillin-streptomycin (v/v). For IVM, COC was incubated in a 4-well dish (30-40 oocytes per well; Falcon, Becton-Dickinson Ltd., Plymouth, UK) for 22 hours in a 38.5° C. and 5% $CO2$ environment in 450 μL TCM-199 tissue culture medium supplemented with 10% FBS, 0.005 AU/ml FSH (Antrin, Teikoku, Japan), 100 μM Cysteamine (Sigma-Aldrich), 1 μg/ml 17β-estradiol (Sigma-Aldrich).

Example 1-3. Sperm Preparation, In Vitro Fertilization (IVF) and Embryo In Vitro Culture (IVC)

Motile sperm were purified and selected using the Percoll gradient method. Briefly, sperm were selected from thawed semen straws by centrifugation on a Percoll discontinuous gradient (45 to 90%) at 1500 rpm for 15 minutes. A 45% Percoll solution was prepared with 1 mL of 90% Percoll (Nutricell, Campinas, SP, Brazil) and 1 mL of capacitation-TALP (Nutricell). The sperm pellet was centrifuged at 1500 rpm for 5 minutes and washed twice with capacitation-TALP. The active motile sperms of the pellet were used for fertilization of mature oocytes (at 24 hours IVM). Oocytes were fertilized with 1 to 2×10⁶ sperm/mL for 18 hours in 30 µL microdrops of IVF-TALP medium (Nutricell) coated with mineral oil in an environment of 38.5° C. and 5% CO2 (day 0). Putative zygotes were removed and cultured in a chemically defined two-step culture medium covered with mineral oil (Sigma-Aldrich). All cultures were performed in an environment of 38.5° C., 5% O2, 5% CO2, and 90% N2. On day 2, division rates were recorded and embryonic development was monitored according to the stages of the International Society for Embryo Transplantation (IETS).

Example 1-4. Microinjection

Transposon DNA was microinjected into the cytoplasm by a microinjection machine (Femtojet Eppendorf, Germany) after removing the cumulus cells of the fertilized oocytes. The amount of injected DNA was 100 ng/mL (1:1 ratio of transposon and transposase). After 7 days, preimplantation stage embryos expressing GFP were selected and transplanted into surrogate mothers.

Example 1-5. Embryo Transfer and Pregnancy Diagnosis

GFP-expressing blastocysts in PBS supplemented with 20% FBS were transferred to the uterine horn of each surrogate mother by a cervical method at day 7 (estrus=0=day of fusion) by a non-surgical approach. The surrogate mothers were examined by rectal examination and ultrasonography on day 45 after estrus to determine embryo survival and pregnancy. Pregnant surrogates were subsequently monitored regularly by rectal examination and ultrasonography.

Fluorescent Cow Production

The cow born by transplantation into the surrogate mother is a cow showing fluorescence, and the fluorescent cow was produced through the above process.

Example 2. Fluorescent Bovine Cell Preparation 2-1. Fluorescent Bovine Cell Primary Culture and Single-Cell Colony Culture The primary cells derived from the ear skin of cow (SNU-F1-2) born by transplanting blastocysts obtained by fertilization of frozen semen of SNU-PB-1 described in Yum S Y et al. Long-term health and germline transmission in transgenic cattle following transposon-mediated gene transfer. BMC Genomics 2018; 19:387 and wild-type cow eggs into a surrogate mother were cultured in DMEM supplemented with 10% bovine fetal serum, 1% penicillin/streptomycin (P/S) (Gibco), 1% non-essential amino acids (NEAA) (Gibco), and 100 mM β(2-ME) (Sigma-Aldrich) in an environment of 38.5° C. and 5% $CO_2$ humidified air. For single-cell colony culture, 100 cells were cultured with cell culture medium in 100 mm cell culture dish (Falcon). On day 10, single-cell colonies were picked up and transported to 12-well plates. When the single-cell colonies were fully grown in 12-well plates, the single-cell colonies were trypsinized for gDNA extraction and stored in Eppendorf tubes.

2-2. sgRNA Synthesis and Transfection

The single guide RNAs (sgRNA) for GFP (Green Fluorescent Protein), PRNP (Prion), and BLG (beta-lactoglobulin) genes were designed by CHOPCOHP software (chopchop.cbu.uib. no/) to select sgRNA candidates for target sites. And these sgRNAs were synthesized by GeneArt™ Precision gRNA Synthesis Kit (Invitrogen).

Cas9 protein (TrueCut™ Cas9 Protein v2, Invitrogen) and sgRNA were transfected into bovine fibroblasts using an electroporation device (program #16, Neon Invitrogen).

Guide Sequence of Sg RNA

| Gene | Guide sequence(5' to 3') | SEQ ID NO |
|---|---|---|
| GFP | CGUCGCCGUCCAGCUCGACC | 161 |
| PRNP | AAAAACCAACAUGAAGCAUG | 102 |
| BLG | GGAGAUGUCGCUGGCCGCCA | 1 |

Example 3. Analysis of the Incidence of Mutations Between the GFP-Expressing Group and the Non-Expressing Group Cas9 protein (Thermo Fisher), GFP guide RNA, and PRNP or BLG guide RNA were delivered to GFP-expressing fibroblasts through transfection. After 5 days, cells in which GFP expression disappeared were identified, and single-cell culture was performed to analyze the mutation rate between the GFP-expressing group and the non-expressing group. The single-cell culture was performed by culturing 150 cells in a 100 mm culture dish. On the 10th day of culture, after checking whether single-cell colonies expressed GFP through a fluorescence microscope, cultured cells were divided into a GFP expression group and a non-expressing group, and each single cell colony was subcultured in a 6-well culture dish. When the culture dish was full of cells, genomic DNA was extracted from each single cell colony. Thereafter, the mutation of PRNP or BLG was confirmed through the T7E1 analysis.

Example 4. T7E1 Analysis

After transfection, genomic DNA was extracted from the cells using a DNA extraction kit (DNeasy Blood & Tissue kit, Qiagen, Limburg, Netherlands). Target locus gene primers were designed by PRIMER3 software (PRNP; Forward: GAGGTGTTCGTTCGTTTTTC(SEQ ID NO: 278), Reverse: CTACCAGTTTCCTGTGCTTA(SEQ ID NO: 279), BLG; Forward: CTTGTCTAAGAGGCTGACCC (SEQ ID NO: 280), Reverse: GAGAAGATGGCTGTCTGCTC (SEQ ID NO: 281)). The PCR reaction was performed under the same conditions. (94° C. 5 minutes, 94° C. 20 seconds/57° C. 30 seconds/72° C. 35 seconds, 72° C. 5 minutes). Mutations in the target locus gene were detected in the T7E1 assay. The T7E1 assay was performed by thawing the amplicon, denaturing, and annealing to make a DNA heteroduplex, which was then subjected to the addition of 5 units of T7 endonuclease 1 (New England Biolabs, Massachusetts, USA) for 15 minutes at 37° C., and then the T7E1 assay was analyzed by 1% agarose gel electrophoresis.

FIG. 4 shows a result showing (a) prion (PRNP) gene knock-out cell ratio and (b) beta-lactoglobulin (BLG) gene knock-out cell ratio in GFP (+) cells and GFP (−) cells. The mutation colony ratio of the prion (PRNP) gene in the GFP negative cell group was higher (90.0% vs. 58.3%) than in the GFP positive cell group. The mutation colony ratio of beta-lactoglobulin (BLG) genes in the GFP negative cell group was higher (79% vs. 58%) than in the GFP positive cell group.

Example 5. Genetically Modified Cow Production Using Bovine Cells Including the GFP Gene 5-1. Egg Collection of Wild-Type Cow and In Vitro Maturation (IVM)

Ovaries are collected in saline at 35° C. in the slaughterhouse and transported to the laboratory within 2 hours. The cumulus-oocyte complex (COC) from follicles with a diameter of 2 to 8 mm is aspirated by using an 18 gauge needle attached to a 10 ml disposable syringe. COCs with evenly granulated cytoplasm and surrounded by three or more layers of compact cumulus cells are selected and washed three times in HEPES buffered tissue culture medium-199 (TCM-199; Invitrogen, Carlsbad, CA, USA) supplemented with 10% FBS, 2 mM NaHCO$_3$(Sigma-Aldrich Corp., St. Louis, MO, USA), and 1% penicillin-streptomycin (v/v). For IVM, COC is incubated in a 4-well dish (30-40 oocytes per well; Falcon, Becton-Dickinson Ltd., Plymouth, UK) for 22 hours in a 38.5° C. and 5% CO2 environment in 450 µL TCM-199 tissue culture medium supplemented with 10% FBS, 0.005 AU/ml FSH (Antrin, Teikoku, Japan), 100 µM Cysteamine (Sigma-Aldrich), 1 µg/ml 17β-estradiol (Sigma-Aldrich).

5-2. Sperm Preparation in GFP-Expressing Bovines, In Vitro Fertilization (IVF) and In Vitro Embryo Culture (IVC)

Motile sperm obtained from cows expressing GFP are purified and selected using the Percoll gradient method. Briefly, sperm are selected from thawed semen straws by centrifugation on a Percoll discontinuous gradient (45-90%) at 1500 rpm for 15 minutes. A 45% Percoll solution is prepared with 1 mL of 90% Percoll (Nutricell, Campinas, SP, Brazil) and 1 mL of capacitation-TALP (Nutricell). The sperm pellet is centrifuged at 1500 rpm for 5 minutes and washed twice with capacitation-TALP. The active motile sperms of the pellet are used for fertilization of mature oocytes (at 24 h IVM). Oocytes are fertilized with 1 to 2×10$^6$ sperm/mL for 18 hours in 30 µL micro drops of IVF-TALP medium (Nutricell) coated with mineral oil in an environment of 39° C. and 5% CO2 (day 0). Putative zygotes are removed and cultured in a chemically defined two-step culture medium covered with mineral oil (Sigma-Aldrich). All cultures are performed in an environment of 38.5° C., 5% O2, 5% CO2, and 90% N2. On day 2, division rates are recorded, and embryonic development is monitored according to the stages of the International Society for Embryo Transplantation (IETS).

5-3. Transformation and Transplantation 5-3-1. Prion (PRNP) Gene Knock-Out Cow Production A single guide RNAs (sgRNA) for GFP (green fluorescent protein) and PRNP (prion) genes are designed by CHOPCOHP software (chopchop.cbu.uib.no/) to select sgRNA candidates for target sites. And these sgRNAs are synthesized by GeneArt™ Precision gRNA Synthesis Kit (Invitrogen). Cas9 protein (TrueCut™ Cas9 Protein v2, Invitrogen) and sgRNA transform fertilized eggs by using an electroporation device (program #16, Neon Invitrogen). Embryos that do not express GFP are selected and transferred to a surrogate mother. The cow born by transplantation into the surrogate mother is a cow in which the prion (PRNP) gene is knocked out, and the prion (PRNP) gene knock-out cow is produced through the above process.

5-3-2. Beta-Lactoglobulin(BLG) Gene Knock-Out Cow Production

A single guide RNAs (sgRNA) for GFP (Green Fluorescent Protein) and BLG (beta-lactoglobulin) genes are designed by CHOPCOHP software (chopchop.cbu.uib.no/) to select sgRNA candidates for target sites. And these sgRNAs are synthesized by GeneArt™ Precision gRNA Synthesis Kit (Invitrogen). Cas9 protein (TrueCut™ Cas9 Protein v2, Invitrogen) and sgRNA transform fertilized eggs by using an electroporation device (program #16, Neon Invitrogen). Embryos that do not express GFP are selected and transferred to a surrogate mother. The cow born by transplantation to the surrogate mother is a cow in which the beta-lactoglobulin (BLG) gene is knocked out, and the beta-lactoglobulin (BLG) gene knock-out cow is produced through the above process.

5-3-3. Loxp-Loxp2272 Knock-In Cow Production

A single guide RNA (sgRNA) for the GFP (green fluorescent protein) gene was designed by CHOPCHOP software (chopchop.cbu.uib.no/) to select sgRNA candidates for the target site. The GFP sgRNA sequence was obtained as a RNA sequence using 5'-cctcgagctggacggcgacg-3' (SEQ ID NO.: 282).

In order to insert the desired gene, loxp-loxp2272, into the position where the GFP gene was edited, ssODN was synthesized in Integrated DNA Technologies (US) company.

The length of the sequence of the gene to be inserted is 79 bp, and the sequence is 5'-ATAACTTCGTATAATGTATGC-TATACGAAGTTATCaCGatCGaCGATAACTTCGTATA GGATACTTTATACGAAGTTAT-3' (SEQ ID NO: 283).

For the GFP gene knock-in experiment, the experiment was divided into three groups: a control group; a group treated with GFP sgRNA and Cas9 protein (knock-out); and a group treated with GFP sgRNA, Cas9 protein, and donor DNA (knock-in).

In the production of fertilized bovine eggs, in vitro fertilization was performed by thawing the frozen semen including the GFP gene. After 18 hours of in vitro fertilization, GFP sgRNA, Cas9 protein (TrueCut™ Cas9 Protein v2, Invitrogen), and donor DNA were transferred to the fertilized egg using an electroporation machine (BEX, GEB 15, Japan).

Thereafter, blastocysts of the cow were produced through culture for 7 days. The presence or absence of expression of the GFP gene was confirmed through a fluorescence microscope (FIG. 5). It was confirmed that the target position of GFP was knocked out (indel generation), or a desired sequence was inserted into the target position, thereby confirming that GFP existing in the genome of a bovine cell was no longer expressed.

By sampling each of these blastocysts, the presence or absence of insertion into the GFP gene was confirmed through PCR. At this time, the GFP primer sequence used for PCR is forward: 5'-GCTCTAGAGCCTCTGCTAA-3' (SEQ ID NO: 284), reverse: 5'-CACAT-GAAGCAGCACGACTTC-3' (SEQ ID NO: 285). The results are shown in FIG. 6 (3,4,5 are knock-out cells, 6,7,8,9 are knock-in cells).

From these results, it can be seen that the engineered bovine cell in which the desired gene-editing, for example, knock-out or knock-in, has occurred, can be easily selected using the bovine cell having the GFP gene of the present disclosure. Without additional complicated screening processes, such as existing antibiotic resistance markers, cells with additional artificial engineering can be easily selected using bovine cells with GFP genes of this disclosure, thereby being used for various research activities using manipulated cells.

This application contains references to amino acid sequences and/or nucleic acid sequences which have been submitted concurrently herewith as the sequence listing text file entitled "000002 us_SequenceListing.TXT", file size 52 kilobytes (KB), created on 4 Jan. 2022. The aforementioned sequence listing is hereby incorporated by reference in its entirety pursuant to 37 C.F.R. § 1.52(e)(5).

What is claimed is:

1. A method for sorting out a bovine cell comprising a modified gene on a target locus in a genome, the method comprising the following steps:
 a) preparing a fluorescent bovine cell,
  wherein the fluorescent bovine cell comprises a fluorescent protein gene on one or more positions in a genome,
  wherein the fluorescent protein gene is a different gene from a gene on the target locus in the genome;
 b) treating a composition to the fluorescent bovine cell,
  wherein the composition comprises
   i) a guide RNA for the fluorescent protein gene, or a nucleic acid encoding the same;
   ii) a guide RNA for the gene on the target locus in the genome, or a nucleic acid encoding the same; and
   iii) a Cas protein, or a nucleic acid encoding the same,
    wherein the guide RNA for the fluorescent protein gene, or the nucleic acid encoding the same; and the guide RNA for the gene on the target locus in the genome, or the nucleic acid encoding the same are simultaneously treated in the fluorescent bovine cell; and
 c) selecting a non-fluorescent bovine cell,
  wherein the non-fluorescent bovine cell comprises a modified gene on the target locus in the genome.

2. The method for sorting out of claim 1, wherein the composition further comprises a transgene to be inserted into the target locus in the genome.

3. The method for sorting out of claim 1, wherein, in the step of preparing the fluorescent bovine cell, a cow comprising the fluorescent protein gene located on 95433564-95434563 position of chromosome 4; 113823097-113823101 position of chromosome 4; and 20085913-20086912 position of chromosome 6 in a genome is used.

4. The method for sorting out of claim 1, wherein, in the step of treating the composition to the fluorescent bovine cell, the composition is in a vector form.

5. The method for sorting out of claim 1, wherein, in the step of treating the composition to the fluorescent bovine cell, the composition is in a RNP (ribonucleoprotein) form.

6. The method for sorting out of claim 1, wherein the modified gene is a beta-lactoglobulin (BLG) gene or a prion (PRNP) gene.

* * * * *